(12) United States Patent
Grotz

(10) Patent No.: US 10,500,059 B2
(45) Date of Patent: Dec. 10, 2019

(54) METHODS OF 3D PRINTING UNIVERSALLY EXPANDING CAGES

(71) Applicant: iOrthopedics, Inc., Las Vegas, NV (US)

(72) Inventor: Robert Thomas Grotz, Las Vegas, NV (US)

(73) Assignee: IORTHOPEDICS, INC., Las Vegas, NV (US)

( * ) Notice: Subject to any disclaimer, the term of this patent is extended or adjusted under 35 U.S.C. 154(b) by 0 days.

(21) Appl. No.: 16/251,014

(22) Filed: Jan. 17, 2019

(65) Prior Publication Data
US 2019/0151112 A1    May 23, 2019

Related U.S. Application Data

(63) Continuation of application No. 16/122,534, filed on Sep. 5, 2018, which is a continuation of application
(Continued)

(51) Int. Cl.
*A61F 2/44* (2006.01)
*A61F 2/46* (2006.01)
*A61F 2/30* (2006.01)

(52) U.S. Cl.
CPC ........... *A61F 2/4425* (2013.01); *A61F 2/446* (2013.01); *A61F 2/447* (2013.01); *A61F 2/4611* (2013.01);
(Continued)

(58) Field of Classification Search
CPC ........ A61F 2/4425; A61F 2/446; A61F 2/447; A61F 2/4611; A61F 2/4637; A61F 2002/30408; A61F 2002/30411; A61F 2002/30507; A61F 2002/30537; A61F 2002/30538; A61F 2002/30545; A61F 2002/30556; A61F 2002/30579;
(Continued)

(56) References Cited

U.S. PATENT DOCUMENTS 5,653,763 A   8/1997   Errico et al.
6,436,142 B1  8/2002   Paes et al.
(Continued)

FOREIGN PATENT DOCUMENTS

WO   WO9848739 A1    11/1998
WO   WO2013181024 A1 12/2013

OTHER PUBLICATIONS

Aryan et al.; Spine surgeons share their needs and challenges; Ortho(R)Know(R); pp. 1-3; Oct. 2014.

*Primary Examiner* — Pedro Philogene
*Assistant Examiner* — David C Comstock
(74) *Attorney, Agent, or Firm* — Michel Graffeo

(57) ABSTRACT

Methods of additive manufacturing expandable medical implants is provided along with methods of patient imaging for 3D printing expandable spine cages and topographically matching patient specific implants. Methods for stabilizing and correcting the alignment of the spine are also provided. Spine pathologies such as lordosis, kyphosis and scoliosis can be corrected with properly expanding spine cages such as those described. Independent control and adjustment of the proximal and distal ends of spine cages allows for treating multiple horizontally affected intervertebral spaces.

17 Claims, 28 Drawing Sheets

Related U.S. Application Data

No. 15/948,982, filed on Apr. 9, 2018, now Pat. No. 10,085,846, which is a continuation of application No. 15/831,192, filed on Dec. 4, 2017, now Pat. No. 9,999,515, which is a continuation of application No. 15/668,650, filed on Aug. 3, 2017, now Pat. No. 9,861,494, which is a continuation of application No. 15/485,131, filed on Apr. 11, 2017, now Pat. No. 9,872,778, which is a continuation of application No. 14/939,905, filed on Nov. 12, 2015, now Pat. No. 9,622,787.

(60) Provisional application No. 62/078,850, filed on Nov. 12, 2014.

(52) U.S. Cl.
CPC .. *A61F 2/4637* (2013.01); *A61F 2002/30408* (2013.01); *A61F 2002/30411* (2013.01); *A61F 2002/30507* (2013.01); *A61F 2002/30537* (2013.01); *A61F 2002/30538* (2013.01); *A61F 2002/30545* (2013.01); *A61F 2002/30556* (2013.01); *A61F 2002/30579* (2013.01); *A61F 2002/30594* (2013.01); *A61F 2002/30841* (2013.01); *A61F 2002/448* (2013.01); *A61F 2002/4642* (2013.01)

(58) Field of Classification Search
CPC .. A61F 2002/30594; A61F 2002/30841; A61F 2002/448; A61F 2002/4642
USPC .......................... 623/17.15, 17.16; 606/246
See application file for complete search history.

(56) References Cited

U.S. PATENT DOCUMENTS

| | | | |
|---|---|---|---|
| 6,821,298 | B1 | 11/2004 | Jackson |
| 6,955,691 | B2 | 10/2005 | Chae et al. |
| 7,819,921 | B2 | 10/2010 | Grotz |
| 7,985,256 | B2 | 7/2011 | Grotz et al. |
| 9,028,550 | B2 | 5/2015 | Shulock et al. |
| 2005/0278036 | A1 | 12/2005 | Leonard et al. |
| 2010/0082109 | A1 | 4/2010 | Greenhalgh et al. |
| 2011/0160861 | A1* | 6/2011 | Jimenez ............ A61B 17/7065 623/17.16 |
| 2014/0180419 | A1 | 6/2014 | Dmuschewsky |
| 2015/0272743 | A1* | 10/2015 | Jimenez ................ A61F 2/447 623/17.16 |
| 2015/0328005 | A1* | 11/2015 | Padovani ............... A61F 2/442 623/17.13 |
| 2016/0166396 | A1 | 6/2016 | McClintock |
| 2017/0119542 | A1* | 5/2017 | Logan .................... A61F 2/442 |
| 2017/0239065 | A9 | 8/2017 | Reimels |

* cited by examiner

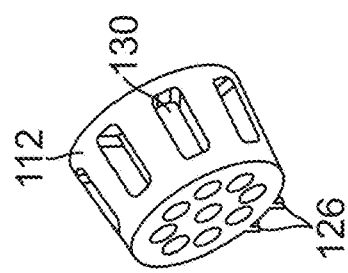
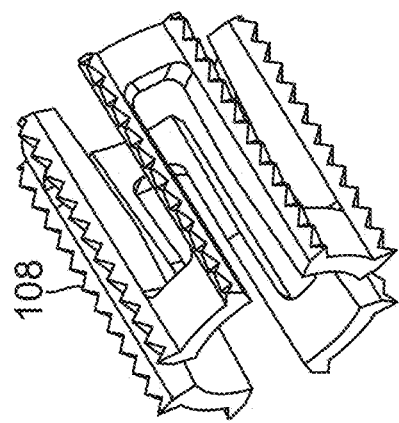
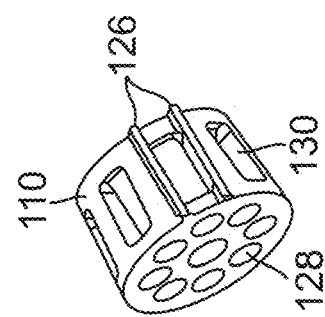
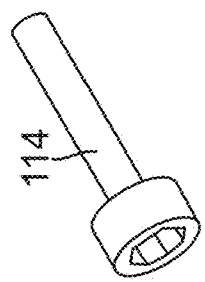
FIG. 5

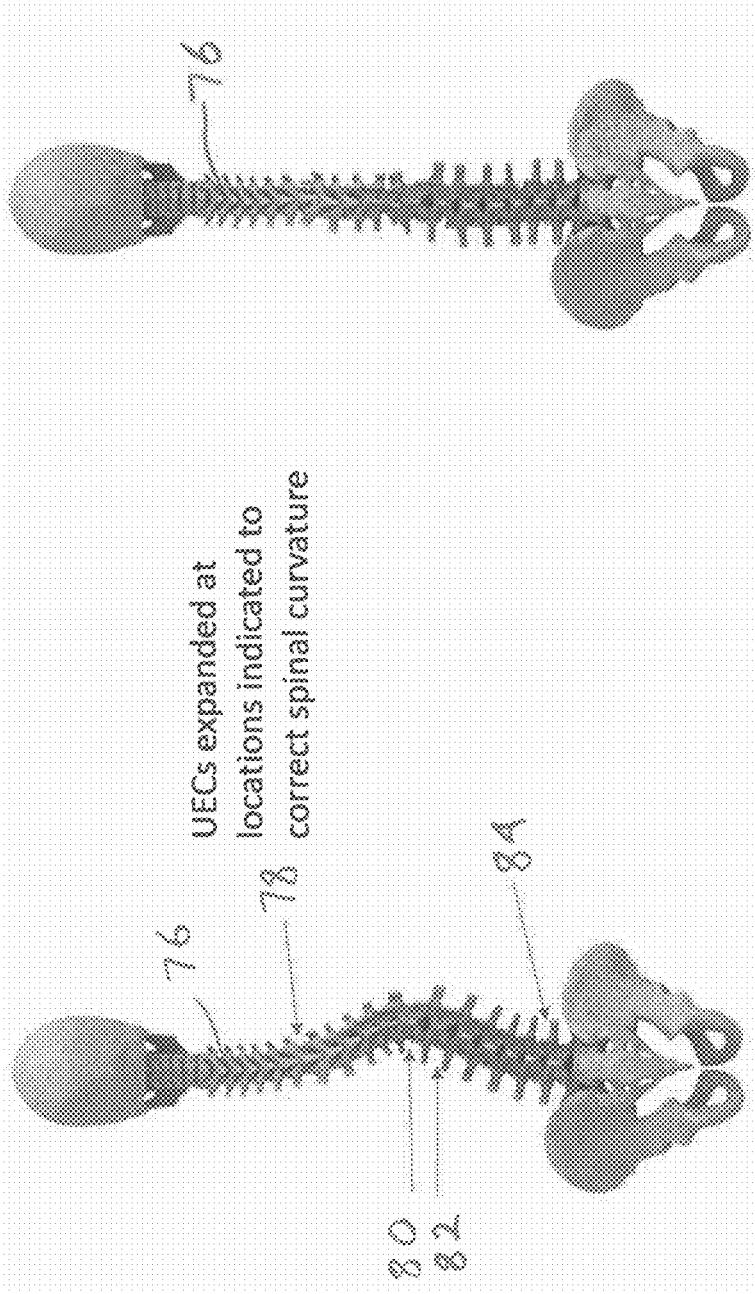

Misalignments

Alignment Restored

METHODS OF 3D PRINTING UNIVERSALLY EXPANDING CAGES

CROSS REFERENCE TO RELATED APPLICATIONS

This application claims benefit of U.S. Non-Provisional patent application Ser. No. 16/122,534 filed Sep. 5, 2018 which claims the benefit of U.S. Non-provisional patent application Ser. No. 15/948,982 filed Apr. 9, 2018 which claims the benefit of U.S. Non-provisional patent application Ser. No. 15/831,192 filed Dec. 4, 2017 now U.S. Pat. No. 9,999,515, which claims the benefit of U.S. Non-provisional patent application Ser. No. 15/668,650 filed Aug. 3, 2017, now U.S. Pat. No. 9,861,494 which claims the benefit of U.S. Non-provisional patent application Ser. No. 15/485,131 filed Apr. 11, 2017, now U.S. Pat. No. 9,872,778 which claims the benefit of U.S. non-provisional patent application Ser. No. 14/939,905 filed Nov. 12, 2015, now U.S. Pat. No. 9,622,878 which claims the benefit of U.S. Provisional Application No. 62/078,850 filed Nov. 12, 2014, all of which are incorporated herein by reference in their entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The present disclosure generally relates to medical devices for stabilizing the vertebral motion segment or other bone segments. More particularly, the field of the disclosure relates to a universally expanding cage (UEC) and method of use for providing controlled spinal correction or other bond segment spacing and/or alignment.

BACKGROUND

Conventional spine cages or implants are typically characterized by a kidney bean-shaped body comprising a hydroxyapatite-coated surface provided on the exterior surface for contact with adjacent vertebral segments or endplates which are shown in FIG. 1. A conventional spine cage with flat endplates is typically inserted posterolaterally proximate to the neuroforamen of the distracted spine after a trial implant creates a pathway. Optionally two parallel externally threaded conduits are inserted anteriorly to achieve lumbar arthrodesis. The implants are often of constant diameter whereas the L5-S1 disc space is trapezoidal, thus a 'flat back' syndrome may be iatrogenically created. Generally spine intradiscal implants are for lumbar fusion or cervical motion preservation, while a separate system of rods and screws corrects alignment.

With the novel UECs disclosed herein, additional options include fusion throughout the spinal column, and deformity angular correction.

Existing devices for interbody stabilization have important and significant limitations. Among the limitations are an inability to expand and distract the endplates. Consequently, if a cage that is "to small" is inserted it can 'rattle around and never heal'. If the static cage is too big, it can injure adjacent nerves or destabilize the spine via end plate resection or subsidence.

Current devices for interbody stabilization include static spacers composed of titanium, PEEK, and high performance thermoplastic polymer produced by VICTREX, (Victrex USA Inc, 3A Caledon Court, Greenville, S.C. 29615), carbon fiber, or resorbable polymers. Current interbody spacers may not maintain interbody lordosis and can contribute to the formation of a straight or even kyphotic segments and the clinical problem of "flatback syndrome." Separation of the endplates increases space available for the neural elements, specifically the neural foramen. Existing static cages do not reliably improve space for the neural elements. Therefore, what is needed is an expanding cage that will increase space for the neural elements posteriorly between the vertebral bodies, or at least maintain the natural bone contours to avoid neuropraxia (nerve stretch) or encroachment.

U.S. Pat. No. 7,985,256, filed Sep. 26, 2006 and titled "Selectively Expanding Spine Cage, Hydraulically Controllable in Three Dimensions for Enhanced Spinal Fusion", and U.S. Pat. No. 7,819,921, filed Oct. 31, 2007 and titled "Linearly expanding spine cage for enhanced spinal fusion", both provide detailed background on expanding spine cages.

The cages disclosed in U.S. Pat. No. 7,985,256 above are restricted to use with hydraulics, and lumbar fusion. The cage disclosed in U.S. Pat. No. 7,819,921 allows for trapezoidal linear expanding, not uniform expansion, thus a trapezoidal L5 cage as disclosed therein will preserve natural lumbar lordosis. The disclosed cage was never developed. It is intended for use as two (2) parallel linearly expanding split conduits inserted anteriorly for lumbar fusion.

In contrast, the UEC cages disclosed herein expands either uniformly, or at either end proximally or distally. Given the adjustment option the surgeon can correct angulation deformity with the novel UEC.

Another problem with conventional devices of interbody stabilization includes poor interface between bone and biomaterial. Conventional static interbody spacers form a weak interface between bone and biomaterial. Although the surface of such implants is typically provided with a series of ridges or coated with hydroxyapetite, the ridges may be in parallel with applied horizontal vectors or side-to-side motion. That is, the ridges or coatings offer little resistance to movement applied to either side of the endplates. Thus, nonunion is common in allograft, titanium and polymer spacers, due to motion between the implant and host bone. Conventional devices typically do not expand between adjacent vertebrae. Since the UEC expands under surgeon control, the visible, palpable 'goodness of fit' setting can ideal lock opposing vertebral endplates at the time of surgery. As healing accrues, the implants become inert. Since no motion equates with no pain, clinical results are improved with UECs.

Therefore, what is needed is a way to expand an implant to develop immediate fixation forces that can exceed the ultimate strength at healing, with improved abilities to enable disc space fixation solidarity while correcting spine angular deformity. Such an expandable implant ideally will maximize stability of the interface and enhance stable fixation. The immediate fixation of such an expandable interbody implant advantageously will provide stability that is similar to that achieved at the time of healing. Such an implant will have valuable implications enhancing early post-operative rehabilitation for the patient.

Another problem of conventional interbody spacers is their large diameter requiring wide exposure. Existing devices used for interbody spacers include structural allograft, threaded cages, cylindrical cages, and boomerang-shaped cages. Conventional devices have significant limitation with regard to safety and efficacy. Regarding safety of the interbody spacers, injury to neural and aortic elements may occur with placement from an anterior or posterior approach. A conventional spine cage lacks the ability to expand, diminishing its fixation capabilities. Prior attempts to preserve lumbar motion have failed by extrusion of the implant after implantation. The risks to neural elements are primarily due to the disparity between the large size of the cage required to adequately support the interbody space, and the small space available for insertion of the device, especially when placed from a posterior or transforaminal approach. Existing boomerang cages are shaped like a partially flattened kidney bean. Their implantation requires a wide exposure and potential compromise of vascular and neural structures, both because of their inability to enter small and become larger, and due to the fact that their insertion requires mechanical manipulation during insertion and expanding of the implant. Once current boomerang implants are prepared for insertion via a trial spacer to make a pathway toward the anterior spinal column, the existing static cage is shoved toward the end point with the hope that it will reach a desired anatomic destination. Given the proximity of nerve roots and vascular structures to the insertion site, and the solid, relatively large size of conventional devices, such constraints predispose a patient to foraminal (nerve passage site) encroachment, and possible neural and vascular injury.

Therefore, what is needed is a minimally invasive expanding spine cage that is capable of insertion with minimal invasion into a smaller aperture. Such a minimally invasive spine cage advantageously could be expanded with completely positional control or adjustment in three dimensions. What is also needed is a smaller expanding spine cage that is easier to operatively insert into a patient with minimal surgical trauma in contrast to conventional, relatively large devices that create the needless trauma to nerve roots in the confined space of the vertebral region. Existing interbody implants have limited space available for bone graft. Adequate bone graft or bone graft substitute is critical for a solid interbody arthrodesis. It would be desirable to provide an expandable interbody cage that will permit a large volume of bone graft material to be placed within the cage and around it, to fill the intervertebral space. Additionally, conventional interbody implants lack the ability to stabilize endplates completely and prevent them from moving. Therefore, what is also needed is an expanding spine cage wherein the vertebral end plates are subject to forces that both distract them apart, and hold them from moving. Such an interbody cage would be capable of stabilization of the motion segment, thereby reducing micromotion, and discouraging pseudoarthrosis (incomplete fusion) and pain.

Ideally, what is needed is a spine cage or implant that is capable of increasing its expansion in height and angle, spreading to a calculated degree. Furthermore, what is needed is a spine cage that can adjust the amount of not only overall anterior posterior expansion, but also medial and lateral variable expansion so that both the normal lordotic curve is maintained, and adjustments can be made for scoliosis or bone defects. Such a spine cage or implant would permit restoration of normal spinal alignment after surgery and hold the spine segments together rigidly, mechanically, until healing occurs.

What is also needed is an expanding cage or implant that is capable of holding the vertebral or joint sections with increased pullout strength to minimize the chance of implant fixation loss during the period when the implant is becoming incorporated into the arthrodesis bone block.

SUMMARY OF THE DISCLOSURE

According to some aspects of the disclosure, an expandable medical implant is provided with an implantable cage body having a proximal end and a distal end.

An expandable medical implant comprising: a cage body comprising a distal end and a proximal end; a central channel or a central bore; and an actuator comprising: a distal end configured to mate with a distal expansion means; and a proximal end configured to mate with a first adjustment tool; wherein the actuator is positioned through the central channel and when rotated in a first direction causes an expansion in the distal end of the cage body and when rotated in a second direction causes a contraction in the distal end of the cage body.

In some embodiments, the cage body has a central bore or channel. In a preferred embodiment, the actuator is accommodated by the central channel of the cage body and coaxial therewith. In a preferred embodiment, the actuator is also accommodated by a proximal expansion means. In one embodiment, the proximal expansion means is a plug. In another embodiment, the actuator is coaxially accommodated by a central opening in the proximal expansion means. In another embodiment, the actuator is coaxially accommodated by a central opening in the proximal expansion means through which central opening the actuator passes to meet with and engage with a distal expansion means. In one embodiment, the distal expansion means is a plug. In one embodiment, a second adjustment tool is configured to engage with the proximal expansion means. In another embodiment, the proximal expansion means comprises a central bore which is configured to engage with a second adjustment tool. In another preferred embodiment, the second adjustment tool is configured to actuate the proximal expansion means. In some aspects, the proximal expansion means causes expansion or contraction of the proximal bone engaging surfaces of the cage body.

In another aspect, the invention provides an expandable medical implant comprising a proximal expansion means. In one embodiment, the proximal expansion means is configured to cause expansion or contraction of the bone engaging surfaces of the proximal part of the cage body. In another aspect, the invention provides an expandable medical implant comprising a distal expansion means. The distal expansion means causes expansion or contraction of the distal bone engaging surfaces of the cage body.

In some embodiments, the expandable medical implant has a first and second adjustment tool. In some embodiments, the first and/or second adjustment tools are manipulated by a surgeon. In some embodiments, the first and/or second adjustment tools are manipulated by another tool used by the surgeon. In a preferred embodiment, the adjustment tools are configured to engage directly or indirectly the expansion means.

The expandable medical implant of claim 1, wherein the actuator is threaded.

In some embodiments, the proximal and distal ends of the cage body are each provided with a tapered or cam portion. The cage body further has a longitudinal axis extending between the proximal end and the distal end of the cage body. The implant may further comprise at least one proximal flexure at least partially located adjacent to the proximal end of the cage body and configured to allow a circumference of the distal end of the cage body to resiliently expand.

The implant may further comprise at least one distal flexure at least partially located adjacent to the distal end of the cage body and configured to allow a circumference of the proximal end of the cage body to resiliently expand. The implant may further comprise a proximal plug member having a tapered portion configured to mate with the tapered portion of the proximal end of the cage body. The proximal plug member may be configured to move longitudinally relative to the cage body from a first position to a second position such that the at least one distal flexure moves and the circumference of the proximal end of the cage body resiliently expands. The proximal plug member may also be configured to move from the second position to the first position such that the circumference of the proximal end resiliently contracts. The implant may further comprise a distal plug member having a tapered portion configured to mate with the tapered portion of the distal end of the cage body. The distal plug member may be configured to move longitudinally relative to the cage body from a third position to a fourth position such that the at least one proximal flexure moves and the circumference of the distal end of the cage body resiliently expands. The distal plug member may also be configured to move from the fourth position to the third position such that the circumference of the distal end resiliently contracts.

In some embodiments, the cage body further comprises a first tapered bore at the proximal end configured to slidably receive the proximal plug member, and a second tapered bore at the distal end configured to slidably receive the distal plug member. The first tapered bore may threadably engage the proximal plug member such that when the proximal plug member is rotated relative to the cage body, the proximal plug member advances in a longitudinal direction relative to the cage body. The second tapered bore may threadably engage the distal plug member such that when the distal plug member is rotated relative to the cage body, the distal plug member advances in a longitudinal direction relative to the cage body.

In some embodiments, the at least one proximal flexure comprises a generally circular and open ended aperture and a pair of generally flexible beam portions extending longitudinally from the aperture. The at least one proximal flexure may include a pair of longitudinally extending beam portions separated by a longitudinally extending gap, wherein the at least one proximal flexure further comprises a connector portion interconnecting proximal ends of the beam portions. The at least one proximal flexure may include a plurality of circumferentially spaced proximal flexures, and the at least one distal flexure may include a plurality of circumferentially spaced distal flexures. The plurality of proximal flexures may be rotationally staggered from the plurality of distal flexures.

In some embodiments, each of the proximal flexures includes a pair of longitudinally extending beam portions separated by a longitudinally extending gap and bridged together by a connector portion interconnecting only proximal ends of the beam portions. Each of the distal flexures may include a pair of longitudinally extending beam portions separated by a longitudinally extending gap and bridged together by a connector portion interconnecting only distal ends of the beam portions. Each of the proximal flexures can share a beam portion with two of the distal flexures that are adjacent to each proximal flexure, thereby forming a continuous serpentine pattern along the cage body.

In some embodiments, the implant includes a first adjustment member coupled to at least the proximal plug member such that when the first adjustment member is rotated, the proximal plug member is caused to move longitudinally. The implant may further include a second adjustment member coupled to the distal plug member such that when the second adjustment member is rotated, the distal plug member is caused to move longitudinally, thereby allowing the proximal and the distal ends of the cage body to be expanded and contracted independent from one another. The first and the second adjustment members may be coaxially nested one within the other and independently rotatable. In some embodiments, the first and the second adjustment members each have knobs axially spaced but adjacent to one another such that the knobs may alternately be rotated in unison or individually. At least one of the first and the second adjustment members may have a keyed end configured to slidably mate and rotationally couple with its associated plug member such that the at least one adjustment member can be removed from the expandable medical implant.

In some embodiments, the cage body has a square or circular cross-section transverse to the longitudinal axis.

In some embodiments, an expandable medical implant includes an implantable cage, a plurality of proximal flexures, a plurality of distal flexures, a proximal plug member, a distal plug member, and first and second adjustment members. In these embodiments, the implantable cage body has a proximal end and a distal end each provided with a threaded and tapered bore. The cage body has a longitudinal axis extending between the proximal end and the distal end of the cage body. The plurality of proximal flexures are circumferentially spaced and each is at least partially located adjacent to the proximal end of the cage body and configured to allow a circumference of the distal end of the cage body to resiliently expand. Each of the proximal flexures comprises a pair of longitudinally extending beam portions separated by a longitudinally extending gap and bridged together by a connector portion interconnecting only proximal ends of the beam portions. The plurality of distal flexures are circumferentially spaced and each is at least partially located adjacent to the distal end of the cage body and configured to allow a circumference of the proximal end of the cage body to resiliently expand. Each of the distal flexures comprises a pair of longitudinally extending beam portions separated by a longitudinally extending gap and bridged together by a connector portion interconnecting only distal ends of the beam portions. Each of the proximal flexures shares a beam portion with two of the distal flexures that are adjacent to each proximal flexure, thereby forming a continuous serpentine pattern along the cage body. The proximal plug member has a threaded and tapered circumference configured to mate with the threaded and tapered bore of the proximal end of the cage body. The proximal plug member is configured to move along the longitudinal axis relative to the cage body from a first position to a second position such that the plurality of distal flexures move and the circumference of the proximal end of the cage body resiliently expands. The proximal plug member is also configured to move from the second position to the first position such that the circumference of the proximal end resiliently contracts. The distal plug member has a threaded and tapered circumference configured to mate with the threaded and tapered bore of the distal end of the cage body. The distal plug member is configured to move along the longitudinal axis relative to the cage body from a third position to a fourth position such that the plurality of proximal flexures move and the circumference of the distal end of the cage body resiliently expands. The distal plug member is also configured to move from the fourth position to the third position such that the circumference of the distal end resiliently contracts. The first adjustment member is rotationally coupled to the proximal plug member such that when the first adjustment member is rotated, the proximal plug member is caused to move along the longitudinal axis. The second adjustment member rotationally coupled to the distal plug member such that when the second adjustment member is rotated, the distal plug member is caused to move longitudinally, thereby allowing the proximal and the distal ends of the cage body to be expanded and contracted independent from one another. The first and the second adjustment members are coaxially nested one within the other and independently rotatable. The first and the second adjustment members each have knobs axially spaced but adjacent to one another such that the knobs may alternately be rotated in unison or individually. At least one of the first and the second adjustment members may have a keyed end configured to slidably mate and rotationally couple with its associated plug member such that the at least one adjustment member can be removed from the expandable medical implant.

According to some aspects of the disclosure, a method of distracting adjacent bone segments having opposing surfaces is provided. The method comprises the steps of inserting an expandable medical implant as described above between the opposing surfaces of the bone segments, and moving the proximal and the distal plug members longitudinally and independently from one another such that the proximal and the distal ends of the cage body expand independently to alter the distance and the angle between the opposing surfaces of the bone segments. In some embodiments, the method further includes the step of removing at least one adjustment member from the medical implant after the adjustment member has been used to move at least one of the proximal and distal plug members. In some embodiments, the bone segments are adjacent vertebrae, and the opposing surfaces are end plates of the adjacent vertebrae.

In some embodiments, the implant includes a proximal end, a distal end, a first adjustment tool and a second adjustment tool wherein the first adjustment tool adjusts one of the proximal end or the distal end of the implant and the second adjustment tool adjusts the other of the proximal end of the implant or the distal end of the implant wherein the first adjustment tool and the second adjustment tool are located at the proximal end of the implant and the first adjustment tool and the second adjustment tool are coaxially nested one within the other and independently rotatable.

In other embodiments, the first adjustment tool adjusts for expansion or contraction of the proximal end of the implant. In some embodiments, the second adjustment tool adjusts for expansion or contraction of the distal end of the implant. In other embodiments, the implant further comprises a cage body, at least one proximal flexure and at least one distal flexure such that the proximal flexure shares a beam portion of the cage body with a distal flexure to form a continuous serpentine pattern along the cage body.

In some aspects, the implant includes a proximal end which is capable of independent resilient expansion by means of a distal flexure, a distal end which is capable of independent resilient expansion by means of a proximal flexure, an expansion means that is functionally associated with the proximal end, an expansion means that is functionally associated with the distal end, an adjustment tool interface that is located at the proximal end, wherein the proximal and distal ends are physically associated by beam portions.

In some other aspects, a first adjustment tool and a second adjustment tool wherein the first adjustment tool adjusts one of the proximal end or the distal end of the implant and the second adjustment tool adjusts the other of the proximal end of the implant or the distal end of the implant.

In other aspects, the first adjustment tool and the second adjustment tool are located at the proximal end of the implant and the first adjustment tool and the second adjustment tool are coaxially nested one within the other and independently rotatable. In some aspects, the first adjustment tool adjusts for expansion or contraction of the proximal end of the implant. In some other aspects, the first adjustment tool adjusts for expansion or contraction of the distal end of the implant. In some other aspects, the second adjustment tool adjusts for expansion or contraction of the proximal end of the implant. In other aspects, the second adjustment tool adjusts for expansion or contraction of the distal end of the implant.

In some aspects, the implant further comprises a cage body, at least one proximal flexure and at least one distal flexure such that the proximal flexure shares a beam portion of the cage body with a distal flexure to form a continuous serpentine pattern along the cage body.

BRIEF DESCRIPTION OF THE DRAWINGS

For the purpose of illustrating concepts of the disclosure, the drawings show aspects of one or more embodiments. However, it should be understood that the present disclosure is not limited to the precise arrangements and instrumentalities shown in the drawings, wherein:

FIGS. 1-3 are a series of lateral representations of two vertebral bodies, wherein FIG. 1 depicts the insertion of an exemplary Universally Expanding Cage (UEC) in its unexpanded state, FIG. 2 depicts the UEC in place between the vertebral bodies and still in its unexpanded state, and FIG. 3 depicts the inserted UEC in its expanded state.

FIG. 5 is an exploded perspective view showing the UEC of FIG. 4.

FIGS. 20A-20C are a series of side views showing the progressive expansion of the UEC of FIG. 16, wherein FIG. 20A shows both ends of the UEC in the unexpanded state, FIG. 20B shows only one end expanded, and FIG. 20C shows both ends expanded.

FIG. 30 is a posterior view showing a human spine exhibiting scoliosis.

FIG. 31 is a posterior view showing the spine of FIG. 29 after being corrected according to aspects of the disclosure.

DETAILED DESCRIPTION

Figure 1:
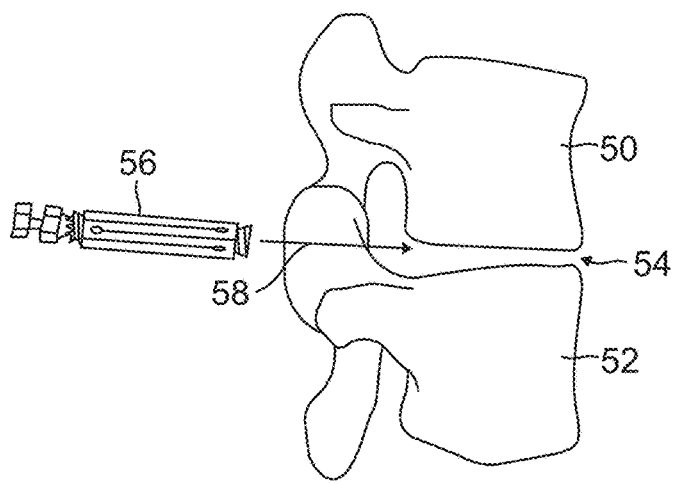
Figure 2:
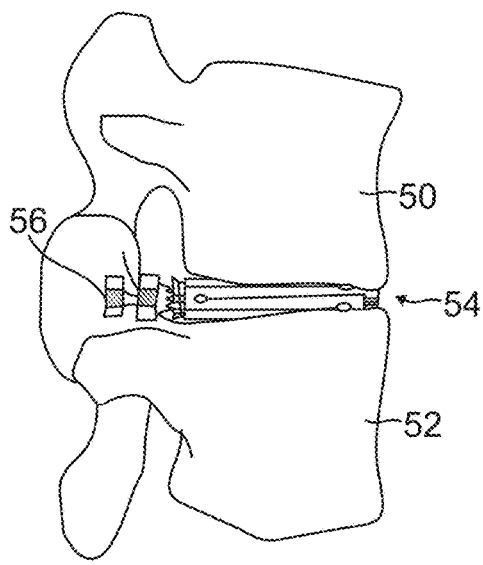
Figure 3:
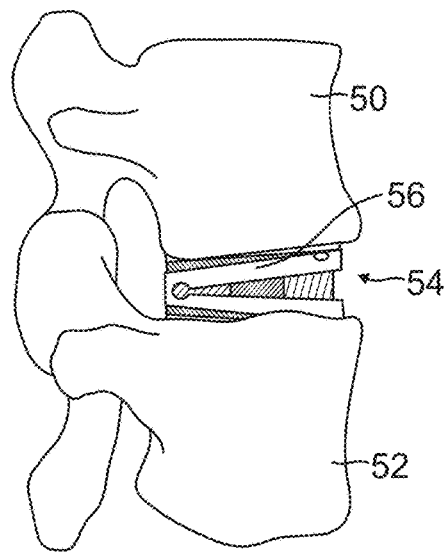

Referring to FIG. 1-3, a series of lateral views of vertebral segments 50 and 52 are shown, depicting the insertion and expansion of one embodiment of UEC (Universally Expanding Cage). The depicted vertebral bodies 50 and 52 have an average 8 mm gap between vertebral end plates, representing an average intervertebral space 54. In a typical implementation, a complete discectomy is performed prior to the insertion of the UEC 56. The intervertebral disc occupying space 54 is removed using standard techniques including rongeur, curettage, and endplate preparation to bleeding subcondral bone. The posterior longitudinal ligament is divided to permit expansion of the intervertebral space.

The intervertebral space 54 may be distracted to about 10 mm using a rotating spatula (not shown). This is a well-known device that looks like a wide screw driver that can be placed into the disc space horizontally and turned 90 degrees to separate the endplates. A novel feature of the UEC is that after intervertebral disc space expansion and preparation (by curetting or ideally arthroscopically facilitated disc material removal), the UEC implant per se can be inserted through any orifice or angle that does not cause injury to nerves or other structures, positioned at the immediate implant location and consequent expansion platform to yield both the best fusion and angular correction results.

In the example implementation depicted in FIGS. 1-3, UEC 56 is inserted posteriorly (in the direction of arrow 58) between vertebral bodies 50 and 52, as shown in FIG. 1. The vertebral space 54 depicted is meant to represent any vertebral space in which it is desired to insert the UEC (sacral, lumbar, thoracic and/or cervical), and from any direction permitted by the surrounding anatomy. In accordance with an aspect of the disclosure, the UEC is reduced to a small size in its unexpanded state to enable it to be inserted through into the intervertebral space 54 as shown in FIG. 1. FIG. 2 shows UEC 56 inserted between vertebral bodies 50 and 52, with UEC 56 still in its unexpanded state. In one exemplary embodiment, dimensions of an unexpanded UEC are: 10-12 mm wide, 10 mm high and 28 mm long to facilitate insertion and thereby minimize trauma to the patient and risk of injury to nerve roots. These dimensions may accommodate the flat external surfaces. Once in place, the exemplary UEC 56 may be expanded to 140 percent of its unexpanded size (as shown in FIG. 3), enabling 20 degrees or more of spinal correction depending on the 3D clinical pre-operation anatomic analysis.

It should be noted that while the exemplary UEC 56 depicted in FIGS. 1-3 is an implant intended to ideally fill the warranted space, other shapes of implants such as those shown in later figures and/or described herein may be used. In various embodiments, the implants may have a transverse cross-section that is circular, oval, elliptical, square, rectangular, trapezoidal, or other shape suited to fill the implant site and transmit the required loads. The implants may straight, curved, bean-shaped, and/or include other shapes and aspect ratios. Additionally, the external surfaces may be smooth, spiked, threaded, coated and/or further adapted as subsequently described in more detail. The UEC can be used at any spinal level the surgeon deems in need of fusion, and may be placed at any position and angle relative to the vertebral endplates as may be needed. One, two, or more UECs may be placed at any particular level to achieve the desired height and angles between vertebral bodies. As will be later described, multiple UECs may be used to adjust the overall cranio-caudal height, the anterior-posterior angle, and the medio-lateral angle between adjacent vertebral bodies. UECs may be implanted at multiple levels to obtain or restore the desired three dimensional curvature and positioning of the spine.

Figure 4:
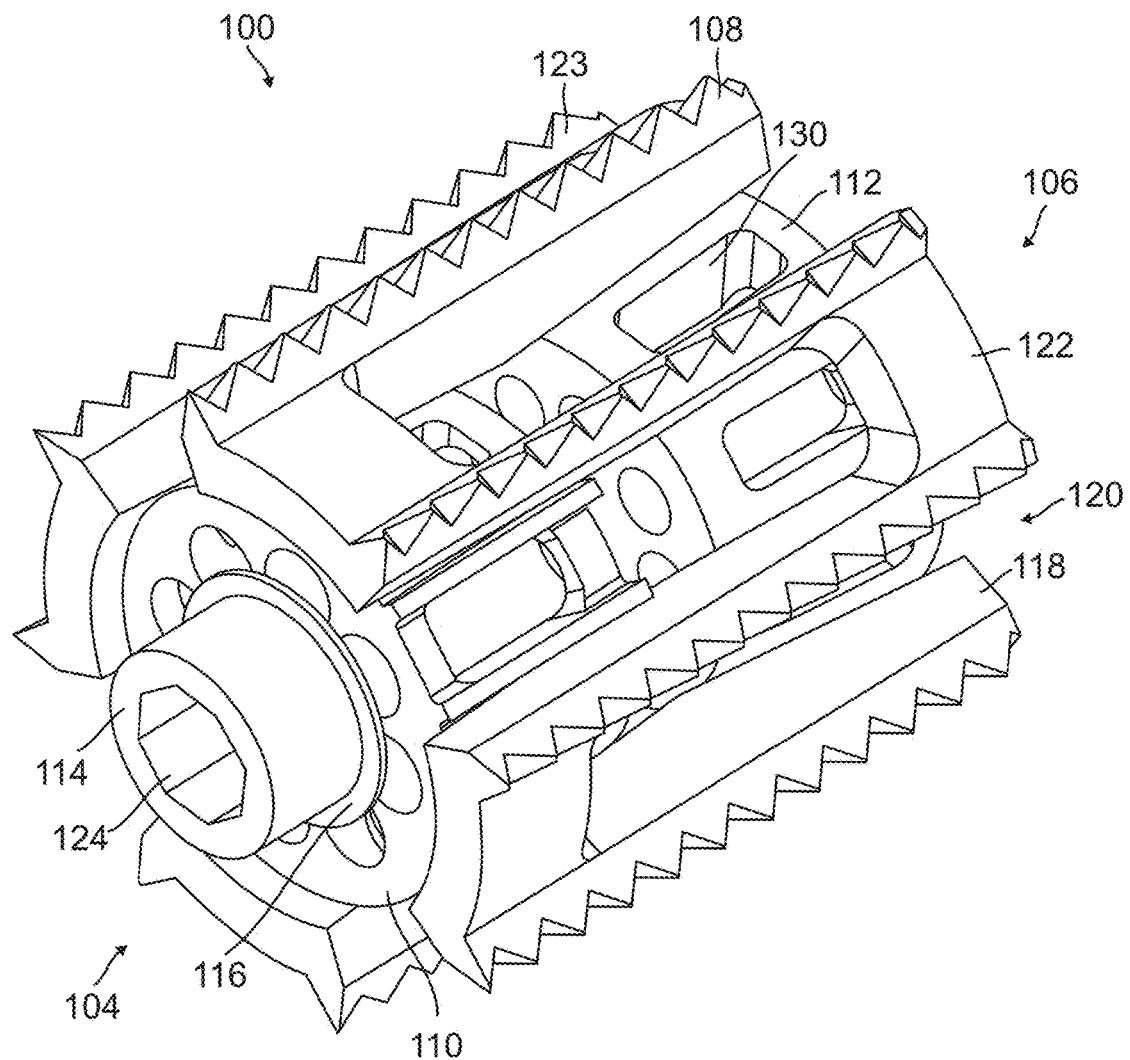
FIG. 4 is a perspective view of a first embodiment of a UEC in an unexpanded state according to aspects of the disclosure.

Referring to FIGS. 4-9, a first embodiment of an exemplary UEC 100 according to aspects of the disclosure is shown. FIG. 4 is an enlarged perspective view which shows details of UEC 100. For ease of understanding, a proximal end 104 and a distal end 106 of UEC 100 can be defined as shown in FIG. 4. It should be noted that while the distal end 106 of UEC 100 is typically inserted first into a patient and proximal end 104 is typically closest to the surgeon, other orientations of this exemplary device and other devices described herein may be adopted in certain procedures despite the distal and proximal nomenclature being used.

Referring to FIG. 5, an exploded perspective view shows the individual components of UEC 100. In this first embodiment, UEC 100 includes a cylindrically-shaped cage body 108, a proximal plug 110, a distal plug 112, a threaded actuator 114, and a washer 116. The terms "plug" and "plug member" are used interchangeably herein. Actuator 114 has a shank sized to slidably pass through a central bore within proximal plug 110 when UEC 100 is assembled. Actuator 114 also has threads on its distal end for engaging with a threaded central bore within distal plug 112. Proximal plug 110 and distal plug 112 each have outer surfaces that are inwardly tapered to match inwardly tapered surfaces within cage body 108 (as best seen in FIG. 9) With this arrangement, actuator 114 may be rotated in a first direction to draw distal plug 112 toward proximal plug 110 to outwardly expand cage body 108, as will be subsequently described in more detail.

Figure 6:
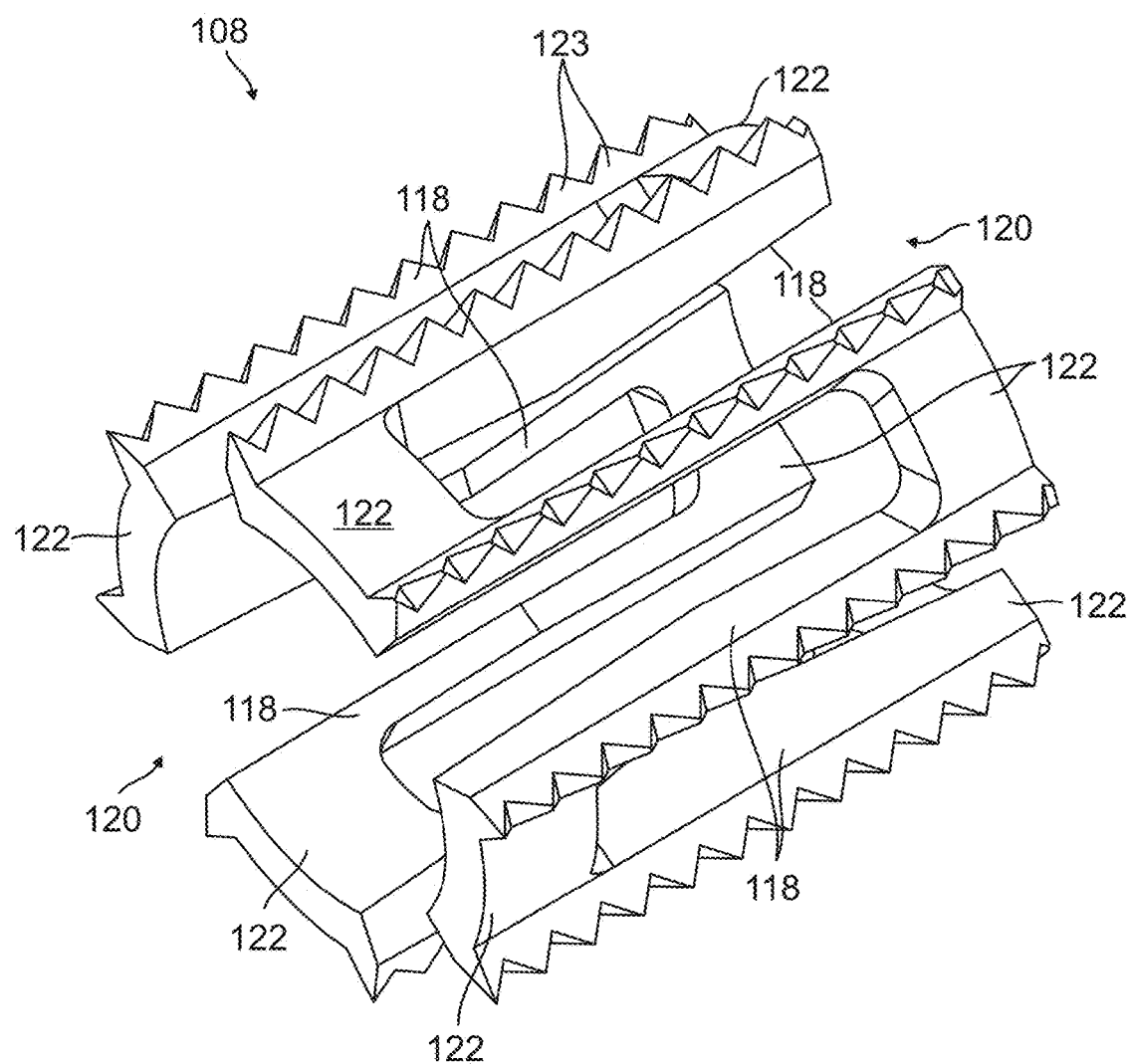
FIG. 6 is a perspective view showing the cage body of the UEC of FIG. 4.

Referring to FIG. 6, this perspective view shows details of cage body 108 of the first exemplary embodiment of UEC 100. In this embodiment, cage body 108 includes eight longitudinally extending beam portions 118, each separated from an adjacent beam portion 118 by a longitudinally extending gap 120. In other embodiments (not shown), the cage body may include fewer or more than eight beam portions, and/or beam portions having a different or varying cross-section or shape. Cage body 108 of the current embodiment also includes eight circumferentially extending connector portions 122. The connector portions 122 interconnect the ends of the beam portions 118. Four of the connector portions 122 are located at the proximal end 104 of cage body 108, and the other four connector portions 122 are located at the distal end 106. The connector portions 122 located at the proximal end 104 are staggered in relation to the connector portions 122 located at the distal end 106 such that each pair of adjacent beam portions 118 are connected at only one end by a connector portion 122. With this arrangement the beam portions 118 and connector portions 122 form a continuous serpentine or repeating S-shaped pattern. The beam portions 118 and or the connector portions 122 are configured to resiliently flex to allow the cage body 108 to increase in diameter when urged radially outward by plugs 110 and 112 (shown in FIG. 4). When plugs 110 and 112 are not urging cage body 108 radially outward, the resiliency of beam portions 118 and or connector portions 122 allows cage body 108 to return to its original reduced diameter. It can be appreciated that as beam portions 118 and or connector portions 122 flex outwardly, gaps 120 become wider at their open ends opposite connector portions 122. The outwardly facing surfaces of beam portions 118 may each be provided with one or more points or spikes 123 as shown, to permit cage body 108 to grip the end plates of the vertebral bodies.

Figure 7:
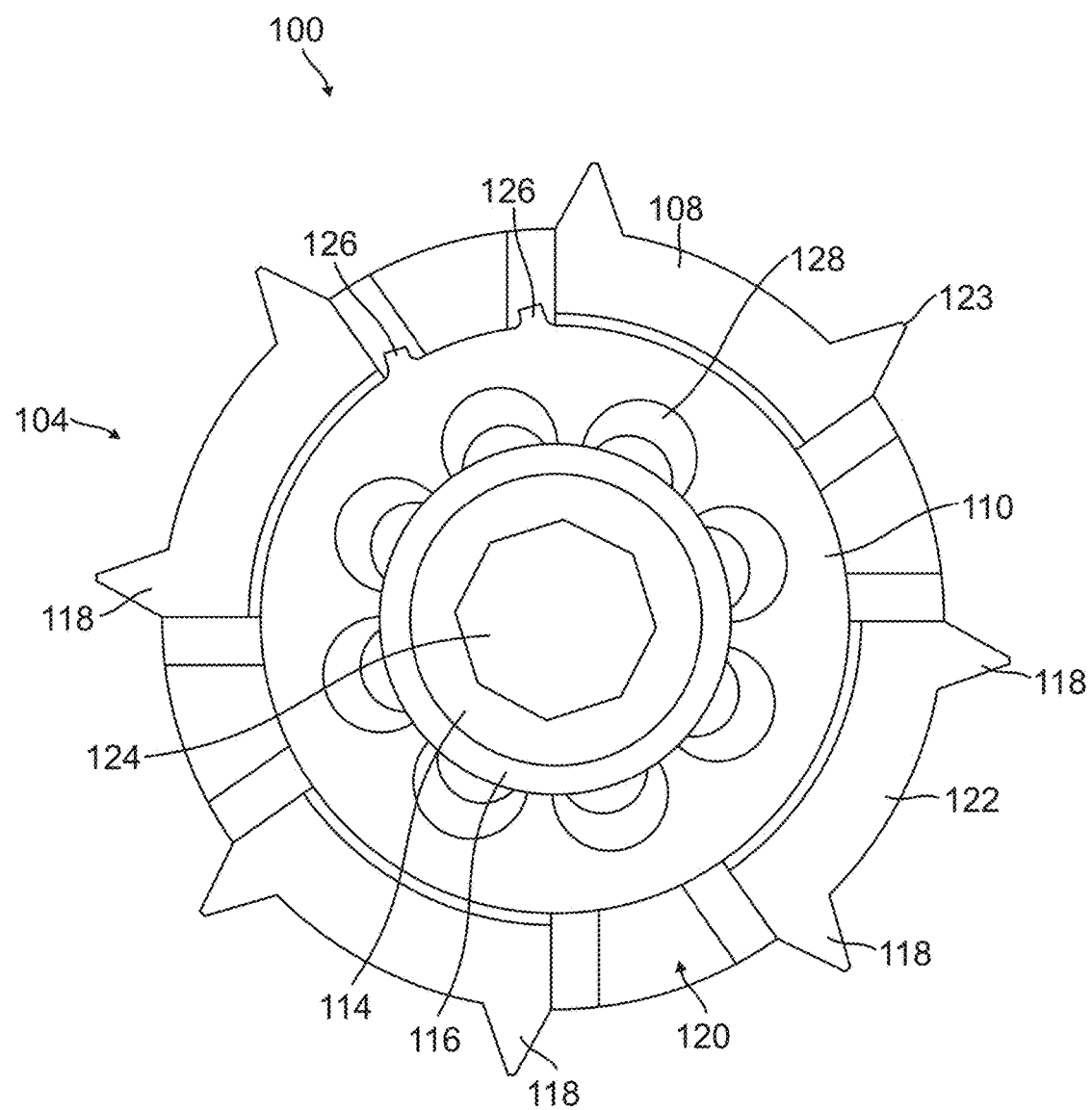
FIG. 7 is a proximal end view of the UEC of FIG. 4.

Referring to FIG. 7, an end view of the proximal end 104 of UEC 100 is shown. The enlarged head at the proximal end of actuator 114 may be provided with a recessed socket 124 as shown for removably receiving a tool for turning actuator 114. Proximal plug 110 (and distal plug 112, not shown) may be provided with radially outwardly extending protuberances 126 that reside in one or more gaps 120 and abut against the side of beam portions 118. This arrangement prevents plugs 110 and 112 from rotating when actuator 114 is turned, thereby constraining plugs 110 and 112 to only move axially toward or away from each other. Proximal plug 110 (and distal plug 112) may be provided with through holes and or recesses 128 to allow for bony ingrowth from the vertebral bodies for more solidly healing/fusing UEC 100 in place. Longitudinally extending slots 130 (shown in FIG. 4) may also be provided for this purpose, and or for packing plugs 110 and 112 with autograft, allograft, and/or other materials for promoting healing/fusion.

Figure 8:
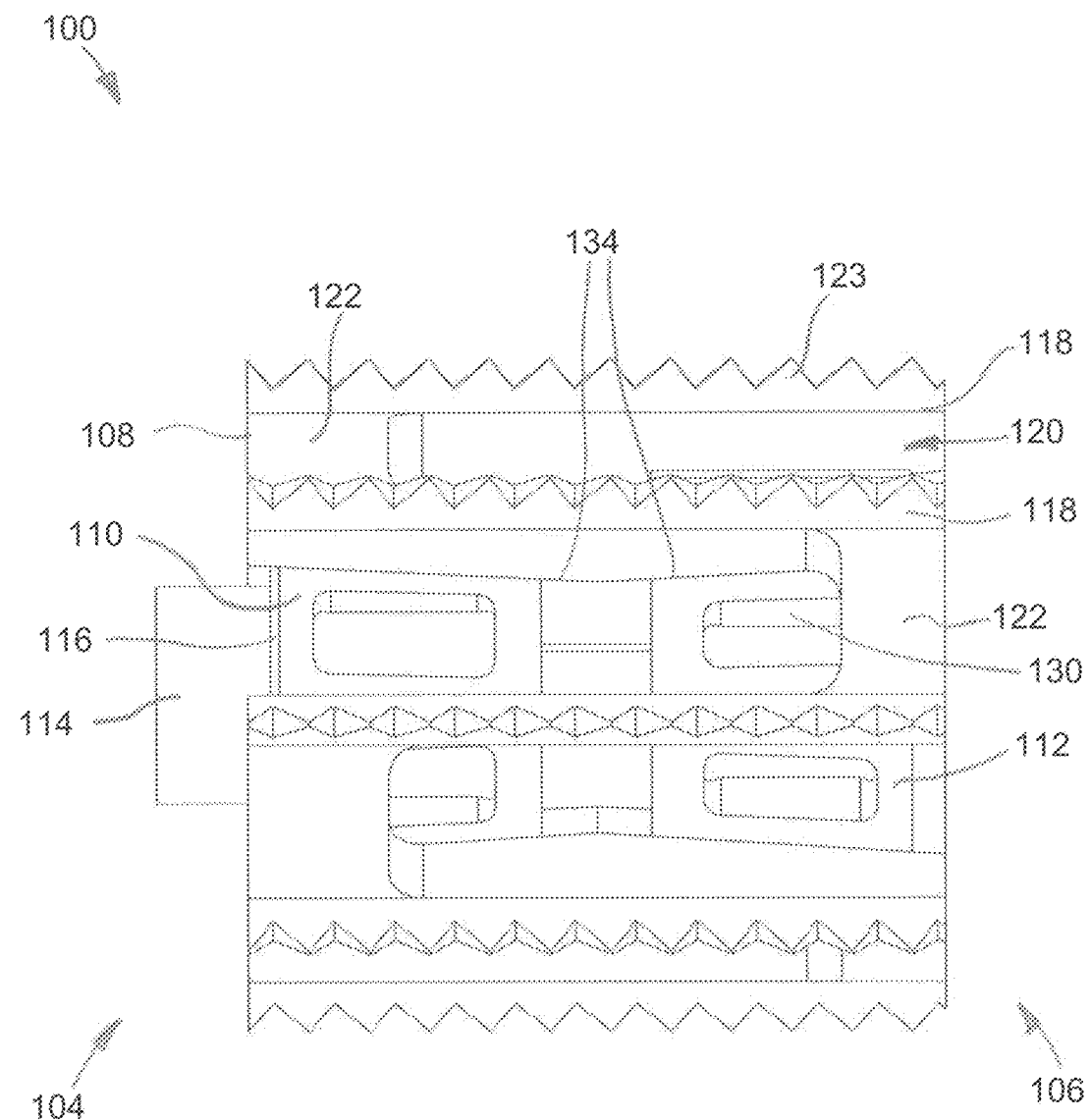
FIG. 8 is a side view of the UEC of FIG. 4.
Figure 9:
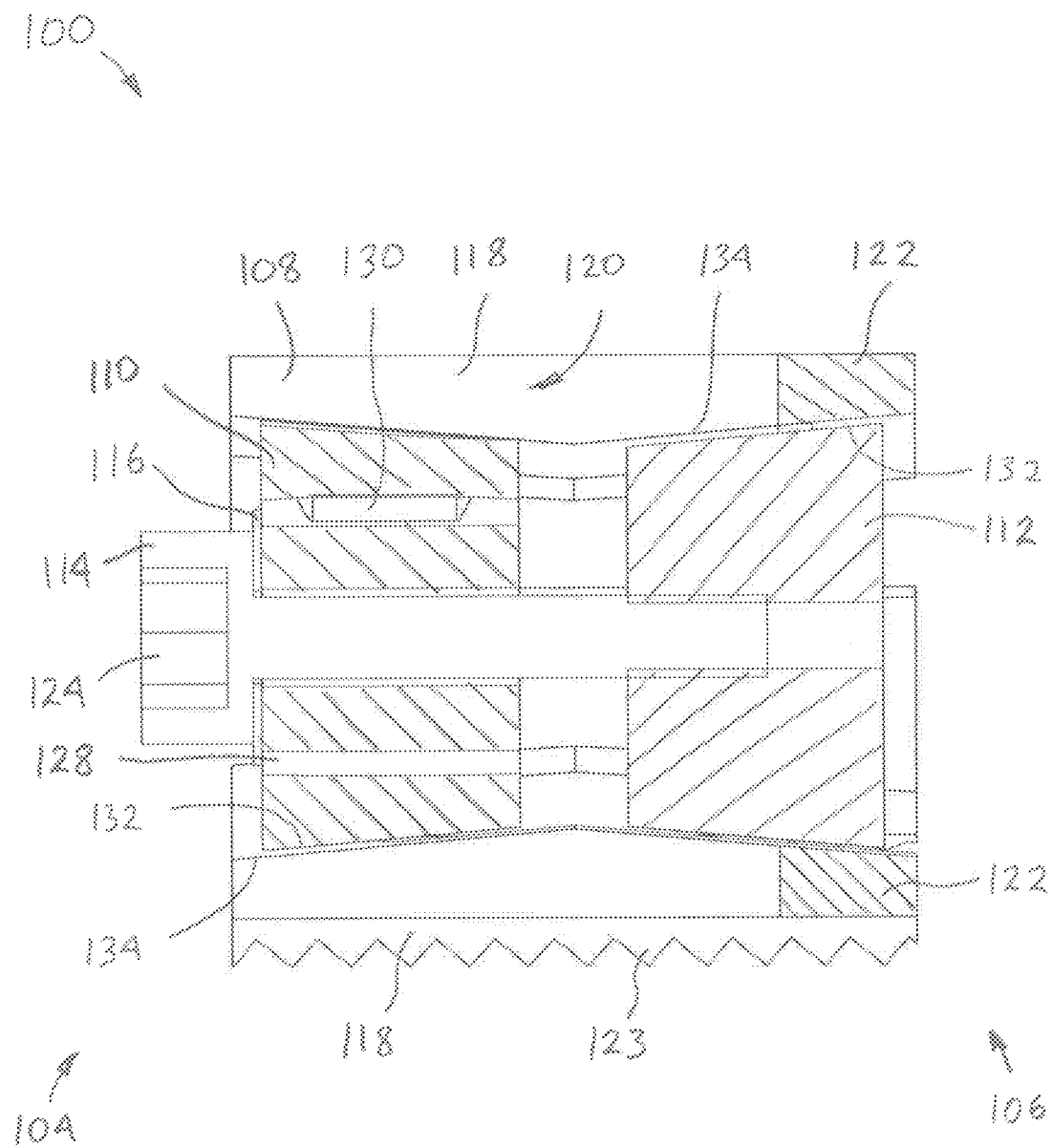
FIG. 9 is a side cross-sectional view of the UEC of FIG. 4.

Referring to FIGS. 8 and 9, a side view and side cross-sectional view, respectively, are shown. In operation, UEC 100 is expanded by inserting a tool such as a hex key wrench or driver (not shown) into the recessed socket 124 at the proximal end of actuator 114 and turning it clockwise. As best seen in FIG. 9, the distal end of actuator 114 is threaded into the central bore of distal plug 112. Turning actuator 114 clockwise causes the distal end of actuator 114 to pull distal plug 112 towards the center of cage body 108 while the enlarged head at the proximal and of actuator 114 pushes proximal plug 110 towards the center. This movement in turn causes the ramped surfaces 132 of plugs 110 and 112 to slide inwardly along the ramped surfaces 134 located along the inside of beam portions 118 and connector portions 122 to cause these elements to flex and expand radially outward as previously described. This process may be reversed by turning actuator 114 counterclockwise. The resilient inward forces from the beam portions 118 and or connector portions 122 (and or the compressive forces from adjacent vertebral bodies) against plugs 110 and 112 causes the two plugs to separate axially, thereby allowing UEC 100 to return to its non-expanded state.

Figure 10:
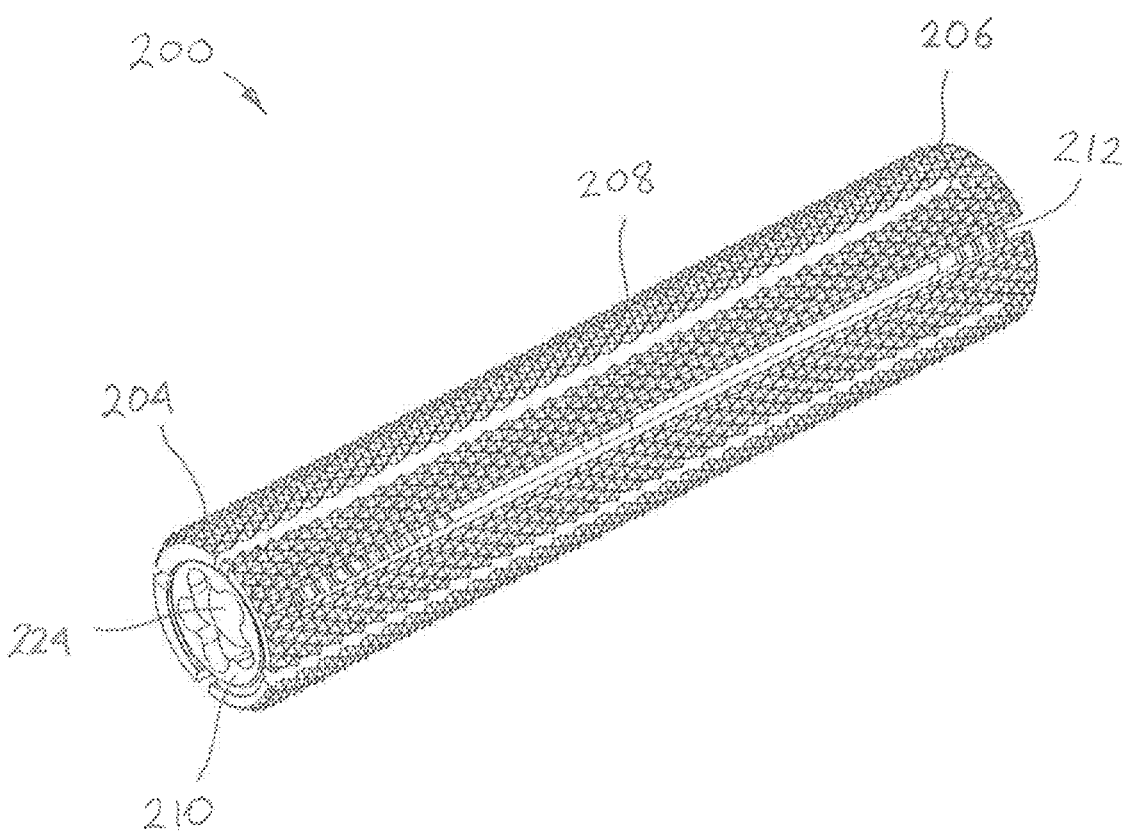
FIG. 10 is a perspective view of a second embodiment of a UEC in an unexpanded state according to aspects of the disclosure.

Referring to FIGS. 10-15, a second embodiment of an exemplary UEC 200 according to aspects of the disclosure is shown. FIG. 10 is a perspective view which shows details of UEC 200. UEC 200 includes a proximal end 204 and a distal end 206, and shares many of the same features of previously described UEC 100, which are identified with similar reference numerals.

Figure 11:
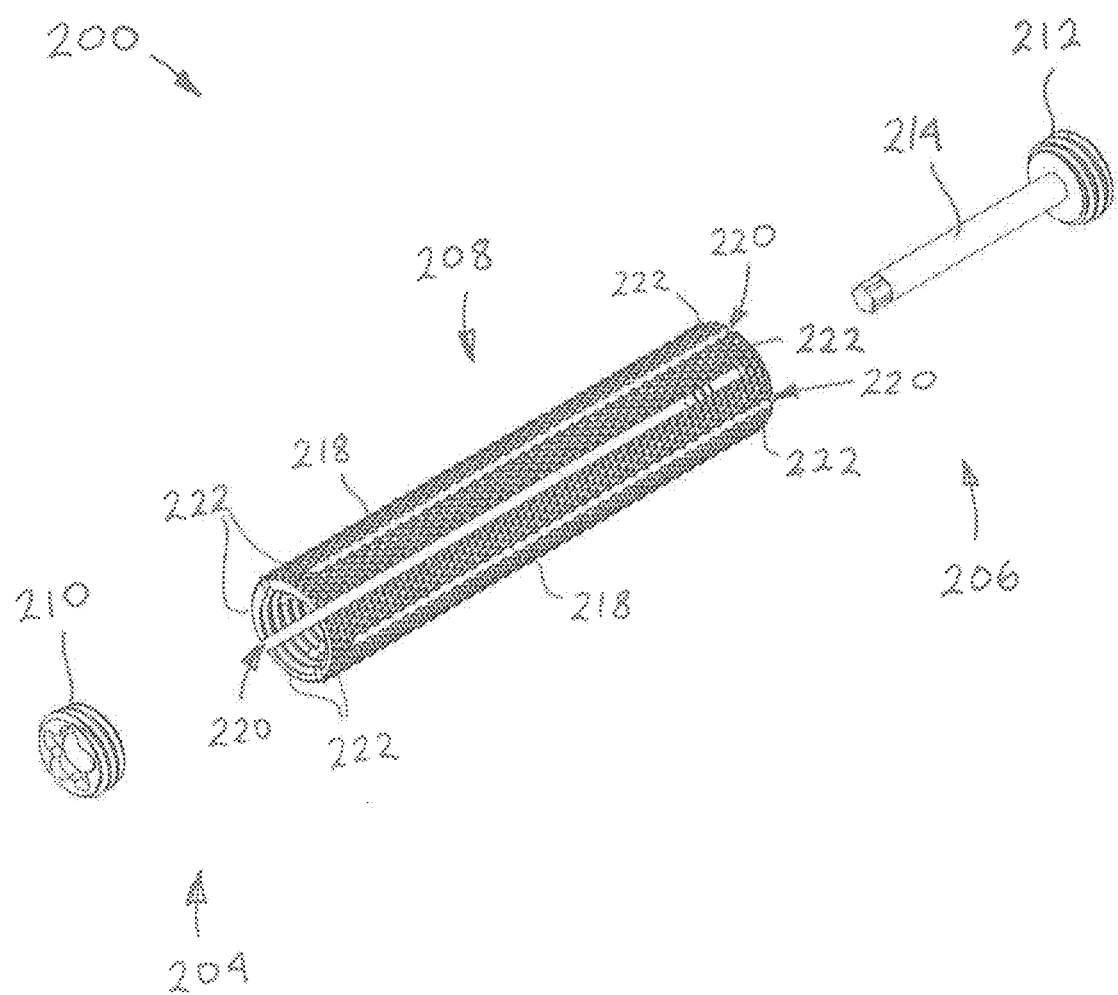
FIG. 11 is an exploded perspective view showing the UEC of FIG. 10.
Figure 15:
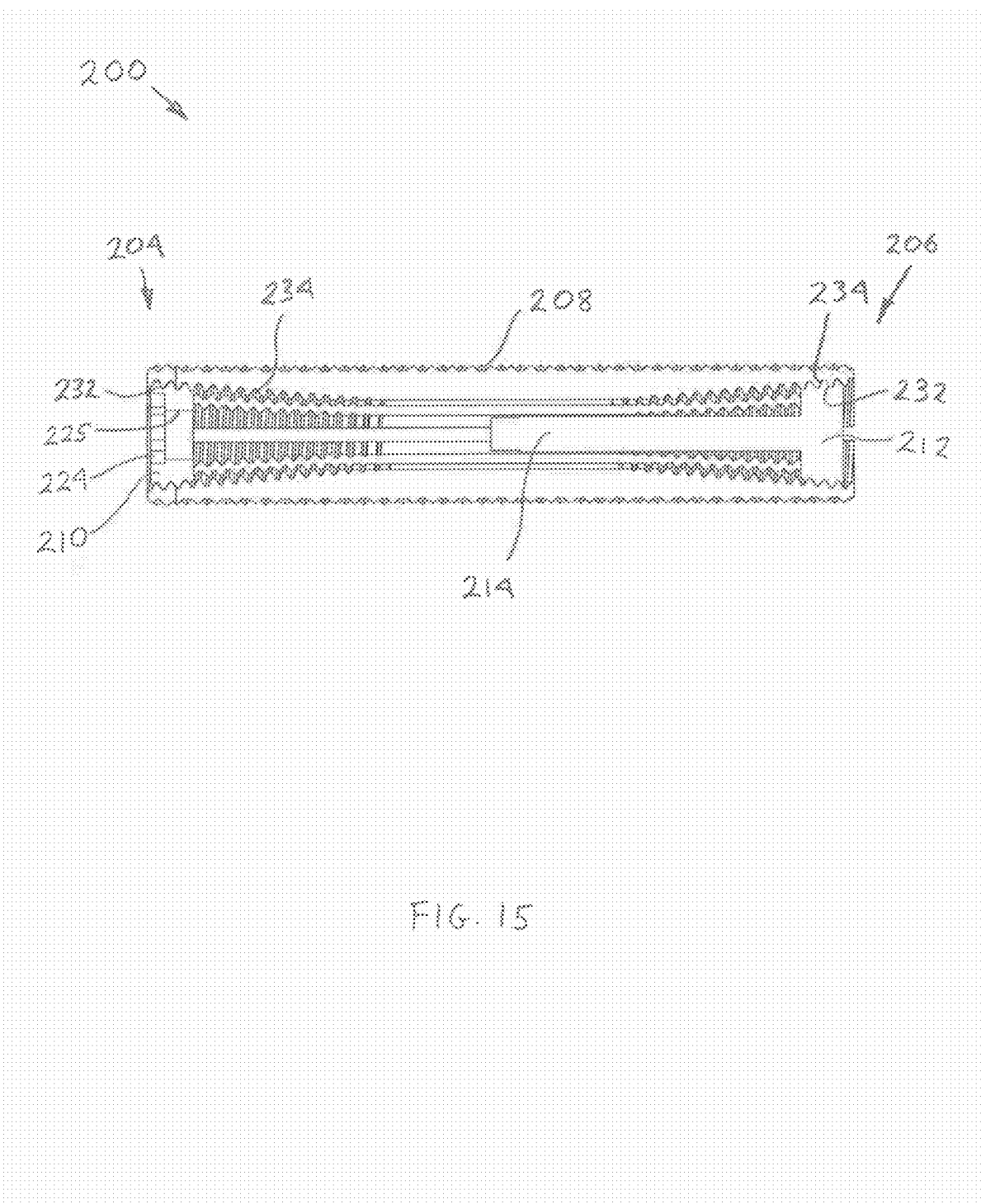
FIG. 15 is a side cross-sectional view showing the UEC of FIG. 10.

Referring to FIG. 11, an exploded perspective view shows the individual components of UEC 200. In this second embodiment, UEC 200 includes an elongated cylindrical cage body 208, a proximal plug 210, and a distal plug 212. Distal plug 212 includes an integrally formed actuator rod 214 that extends along the internal central axis of cage body 208 towards proximal plug 210 when UEC 200 is assembled. Proximal plug 210 and distal plug 212 each have outer surfaces that are threaded and inwardly tapered to match threaded and inwardly tapered surfaces within cage body 208 (as best seen in FIG. 15). With this arrangement, each plug 210 and 212 may be independently rotated to move the particular plug axially toward the middle of cage body 208 to outwardly expand that particular end 204 or 206 of cage body 208, as will be subsequently described in more detail.

Figure 12:
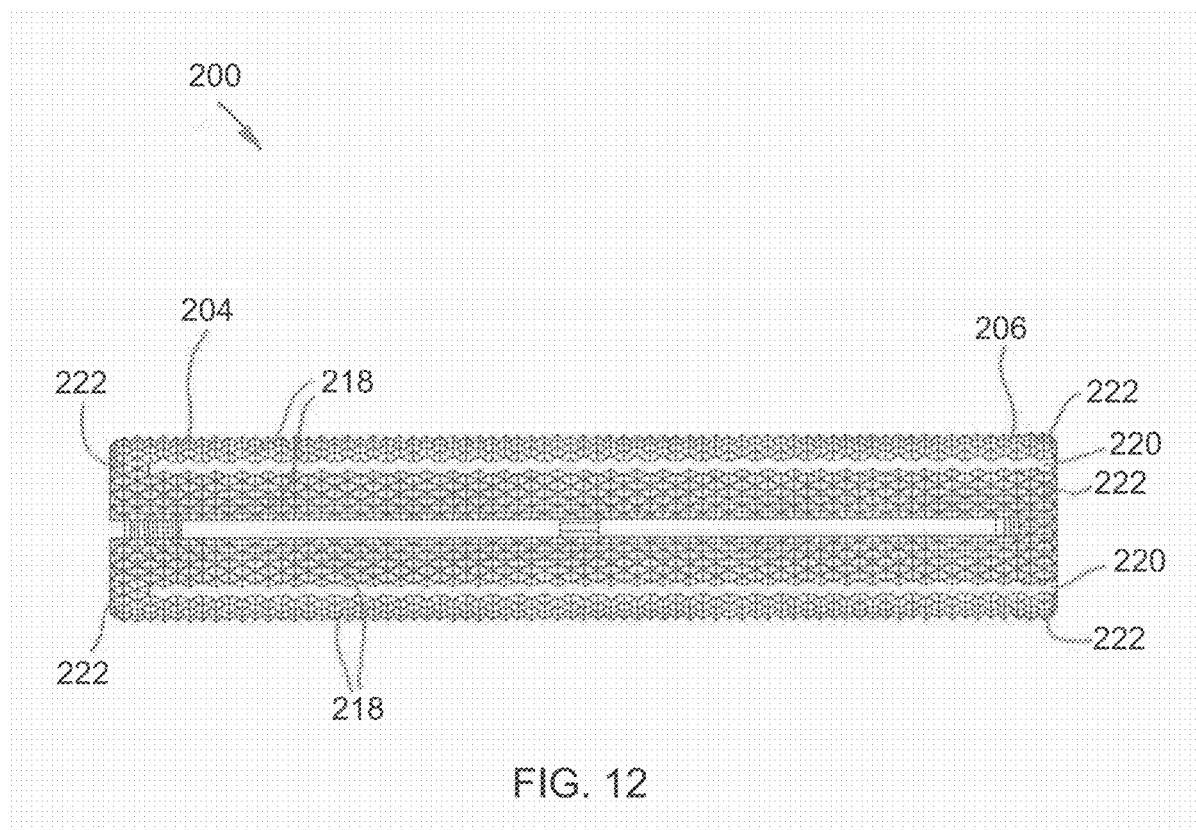
FIG. 12 is a side view showing the UEC of FIG. 10.

As shown in FIGS. 11 and 12, cage body 208 includes eight longitudinally extending beam portions 218, each separated from an adjacent beam portion 218 by a longitudinally extending gap 220. In other embodiments (not shown), the cage body may include fewer or more than eight beam portions, and/or beam portions having a different or varying cross-section or shape. Cage body 208 of the current embodiment also includes eight circumferentially extending connector portions 222. The connector portions 222 interconnect the ends of the beam portions 218. Four of the connector portions 222 are located at the proximal end 204 of cage body 208, and the other four connector portions 222 are located at the distal end 206. The connector portions 222 located at the proximal end 204 are staggered in relation to the connector portions 222 located at the distal end 206 such that each pair of adjacent beam portions 218 are connected at only one end by a connector portion 222. With this arrangement the beam portions 218 and connector portions 222 form a continuous serpentine or repeating S-shaped pattern. The beam portions 218 and or the connector portions 222 are configured to resiliently flex to allow the cage body 208 to increase in diameter when urged radially outward by plugs 210 and 212. When plugs 210 and 212 are not urging cage body 208 radially outward, the resiliency of beam portions 218 and or connector portions 222 allows cage body 208 to return to its original reduced diameter. It can be appreciated that as beam portions 218 and or connector portions 222 flex outwardly, gaps 220 become wider at their open ends opposite connector portions 222. The outwardly facing surfaces of beam portions 218 may each be provided with one or more points or spikes 223 as shown, to permit cage body 208 to grip the end plates of the vertebral bodies.

Figure 13:
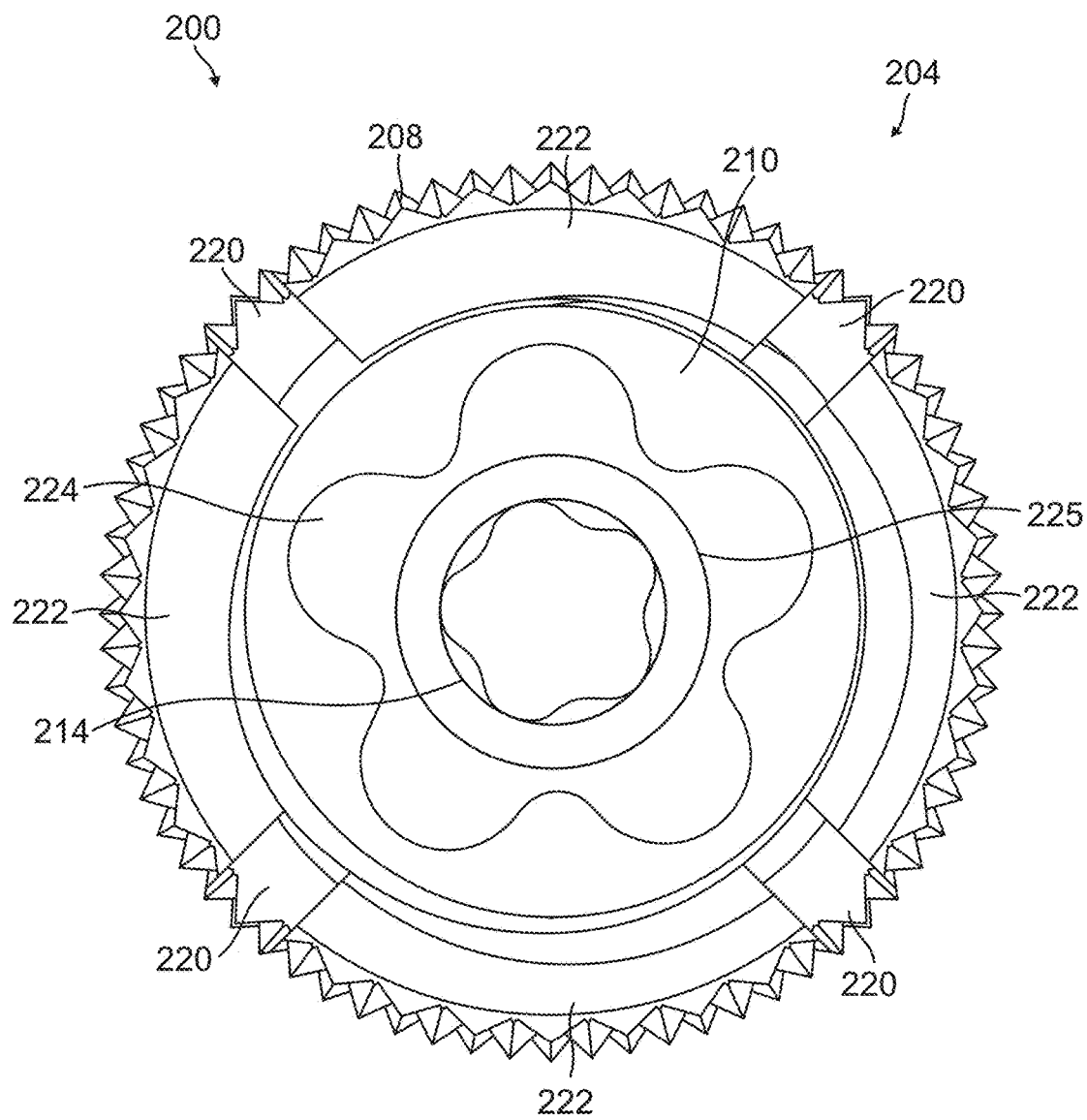
FIG. 13 is a proximal end view showing the UEC of FIG. 10.

Referring to FIG. 13, an end view of the proximal end 204 of UEC 200 is shown. The proximal plug 210 may be provided with a recessed socket 224 as shown for removably receiving a tool for turning proximal plug 210 in either direction, such as a five-lobed driver (not shown). Alternatively, other suitable types of recessed sockets, slots, protruding and/or keyed features may be utilized with a mating driver. The proximal end of actuator shaft 214 (which extends proximally from distal plug 212 inside cage body 208) may be accessed through a central bore 225 in proximal plug 210. The proximal end of actuator shaft 214 may be shaped as shown to be received within a mating driver socket (such as a five-lobed socket, not shown), which can be removably extended into the center of cage body 208 through central bore 225. With this arrangement, both the proximal plug 210 and the distal plug 212 can be independently accessed and rotated from the proximal end of UEC 200 so that the proximal end 204 and the distal end 206 of UEC 200 can be expanded or contracted independently.

Figure 14:
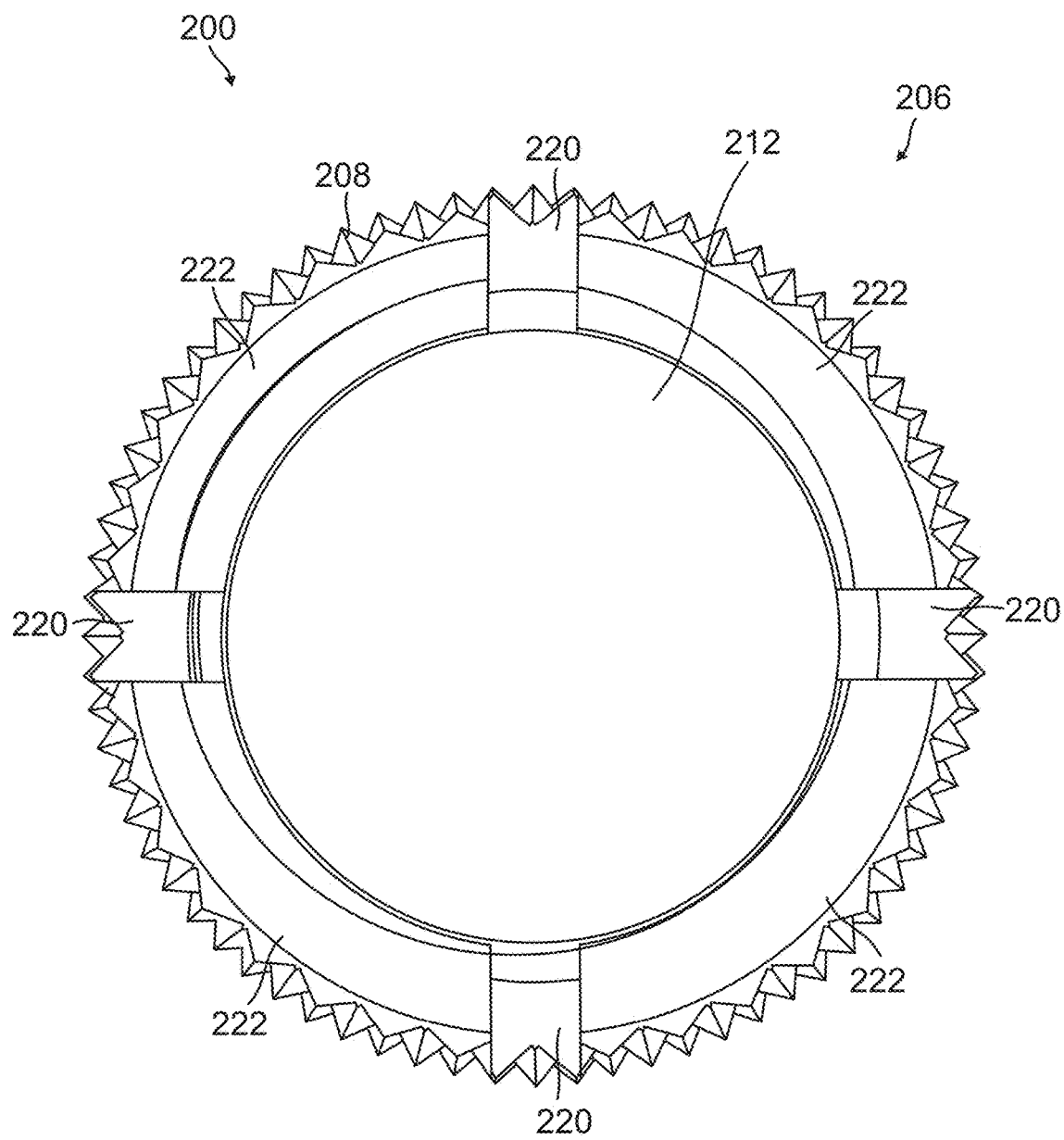
FIG. 14 is a distal end view showing the UEC of FIG. 10.

Referring to FIG. 14, an end view of the distal end 206 of UEC 200 is shown. By comparing FIGS. 13 and 14, it can be appreciated that connector portions 222 at the proximal end 204 of UEC 200 are staggered (i.e. rotated 45°) in relation to the connector portions 222 at the distal end 206 of UEC 200.

Referring to FIG. 15, a side cross-sectional view of UEC 200 is shown. In operation, the proximal end 204 of UEC 200 may be independently expanded by inserting a tool such as a five-lobed driver (not shown) into the recessed socket 224 of proximal plug 210 and turning it clockwise. Turning proximal plug 210 clockwise causes the threaded ramped surfaces 232 of plug 210 to translate inwardly (to the right in FIG. 15) along the threaded ramped surfaces 234 located along the inside of beam portions 218 and connector portions 222 to cause these elements to flex and expand radially outward as previously described. This process may be reversed by turning proximal plug 210 counterclockwise, thereby allowing the proximal end 204 of UEC 200 to return to its non-expanded state. Similarly, the distal end 206 of UEC 200 may be independently expanded by inserting a tool such as a five-lobed socket (not shown) through the central bore 225 in proximal plug 210 until it engages with the proximal end of actuator 214, which is attached to distal plug 212. Turning distal plug 212 counterclockwise (from the perspective of the proximal end) causes the threaded ramped surfaces 232 of plug 212 to translate inwardly (to the left in FIG. 15) along the threaded ramped surfaces 234 located along the inside of beam portions 218 and connector portions 222 to cause these elements to flex and expand radially outward as previously described. This process may be reversed by turning distal plug 212 clockwise, thereby allowing the distal end 206 of UEC 200 to return to its non-expanded state.

The adjustment tools described above (not shown) for turning proximal plug 210 and distal plug 212 may be inserted one at a time into UEC 200. Alternatively, the two tools may be nested together, with the tool for turning the distal plug 212 passing through a central bore in the tool for turning the proximal plug, as will be subsequently shown and described in relation to other embodiments. With this arrangement, both tools may be turned simultaneously or individually. In some embodiments, both proximal plug 210 and distal plug 212 are provided with right-handed threads, so that when both tools are simultaneously turned in the same direction, one end of UEC 200 expands while the other end contracts, thereby changing the outer surface angle of UEC 200 without substantially changing its overall diameter (i.e. without substantially changing the diameter or height of the midpoint of UEC 200.) For example, by turning the two tools in the same direction, the lordotic angle between two vertebral bodies can be changed by UEC 200 without substantially changing the height between the two vertebral bodies.

In other embodiments, one of the plugs 210 or 212 may be provides with a right-handed thread and the other plug provided with a left-handed thread. In these embodiments, when both adjustment tools are simultaneously turned in the same direction, both ends 204 and 206 of UEC 200 expand or contact together without substantially changing the outer surface angle of UEC 200. For example, by turning the two tools in the same direction, the height between the two vertebral bodies can be changed by UEC 200 without substantially changing the lordotic angle between two vertebral bodies.

In some embodiments, plugs 210 and 212 may each be provided with threads having a different pitch from the other. Such an arrangement allows both the height and the angle between adjacent vertebral bodies to be adjusted simultaneously in a predetermined relationship when both adjustment tools are turned together in unison. For example, proximal plug 210 may be provided with right-handed threads of a particular pitch while distal plug 212 may be provided with finer, left-handed threads having half the pitch of the proximal plug threads. In this embodiment, when both adjustment tools are turned together in a clockwise direction, both ends of UEC 200 expand at the same time but the proximal end 204 expands at twice the rate of the distal end 206. This allows the surgeon to increase the height between adjacent vertebral bodies and at the same time angle the bodies away from him or her. One or both of the tools may then be turned individually to more finely adjust the height and angle between the vertebral bodies.

In some embodiments the above-described adjustment tools may be removed from UEC 200 before the surgical procedure is completed. In some embodiments the above adjustment tools may remain in place after the procedure is completed.

In some embodiments. UEC 200 is 50 mm long, has an unexpanded diameter of 10 mm, and an expanded diameter of 14 mm. In other embodiments, the UEC may be configured to expand to about 11, 12, or 13 mm, or more than 14 mm. In still other embodiments, the UEC may be configured with dimensions larger or smaller than these to conform to a particular anatomy or procedure.

Figure 16:
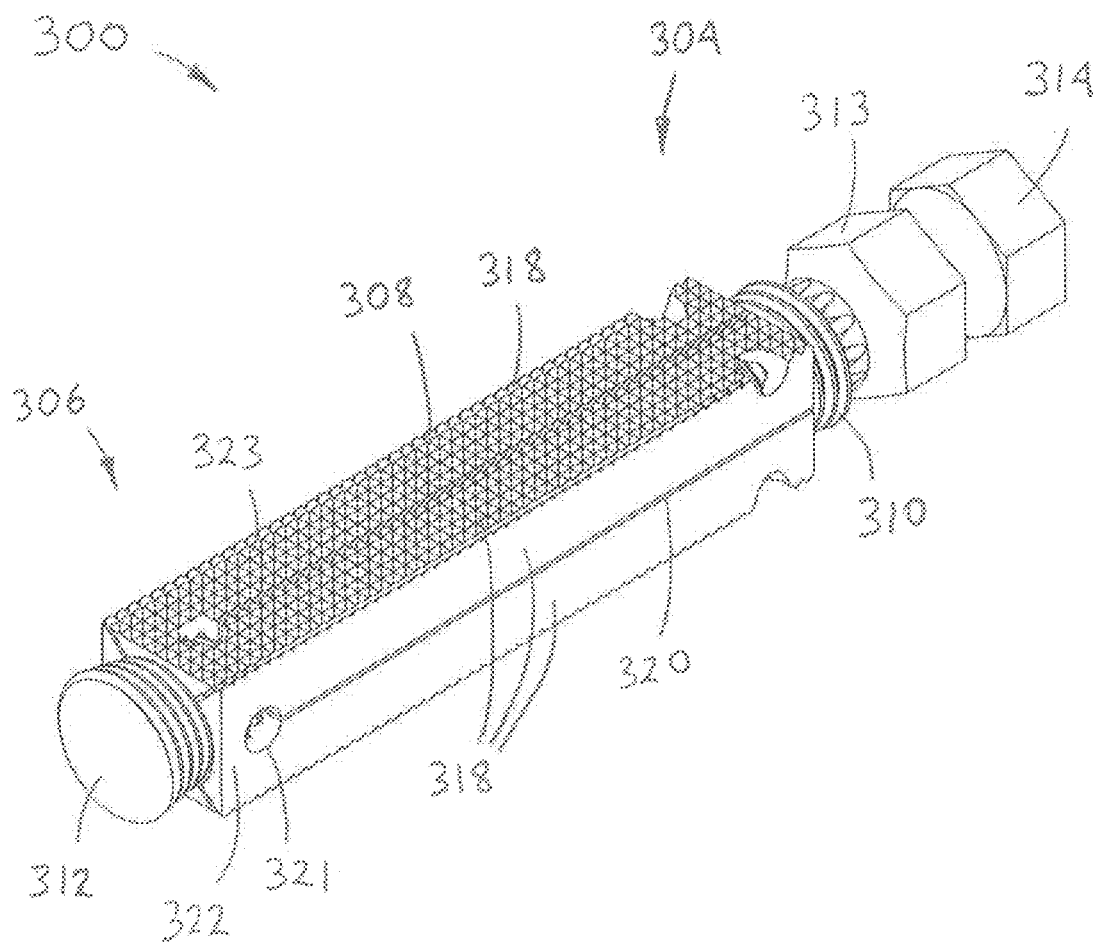
FIG. 16 is a perspective view of a third embodiment of a UEC in an unexpanded state according to aspects of the disclosure.

Referring to FIGS. 16-20, a third embodiment of an exemplary UEC 300 according to aspects of the disclosure is shown. FIG. 16 is a perspective view which shows details of UEC 300. UEC 300 includes a proximal end 304 and a distal end 306, and shares many of the same features of previously described UECs 100 and 200, which are identified with similar reference numerals.

Figure 17:
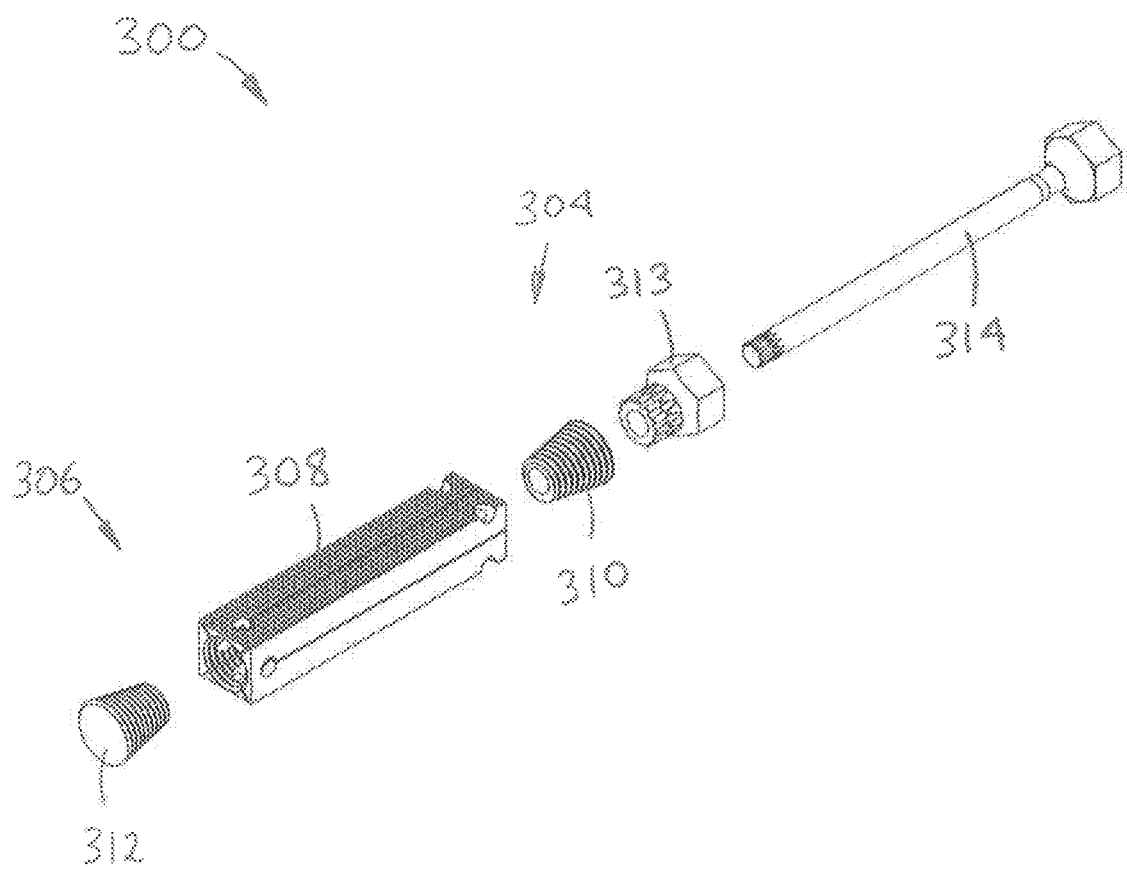
FIG. 17 is an exploded perspective view showing the UEC of FIG. 16.

Referring to FIG. 17, an exploded perspective view shows the individual components of UEC 300. In this third embodiment, UEC 300 includes a rectangular cage body 308, a proximal plug 310, a distal plug 312, a proximal plug adjustment tool 313, and a distal plug adjustment tool 314. As in the previously described UEC 200, both plugs 310 and 312 are threaded and tapered, and each end of cage body 308 is provided with an inwardly tapered and threaded bore configured to receive one of the plugs 310 or 312. Adjustment tools 313 and 314 are similar in construction and operation to the adjustment tools previously described (but not shown) in reference to UEC 200. Proximal plug 310 includes a mating recess on its proximal end (not shown)

configured to removably receive the splined distal end of proximal plug adjustment tool 313 for rotating proximal plug 310. Distal plug 312 includes a smaller mating recess on its proximal end (not shown) configured to removably receive the smaller splined distal end of distal plug adjustment tool 314 for rotating distal plug 312. Both proximal plug adjustment tool 313 and proximal plug 312 are provided with central bores that permit the distal end of distal plug adjustment tool 314 to pass therethrough, through the center of cage body 308, and partially into distal plug 312. In this exemplary embodiment, the proximal ends of adjustment tools 313 and 314 each have a hexagonally-shaped head that permits them to be turned together in unison or individually (as previously described in relation to UEC 200), using wrench(es), socket(s) (not shown) and/or by hand.

As shown in FIGS. 16 and 17, cage body 308 includes eight longitudinally extending beam portions 318, each separated from an adjacent beam portion 318 by a longitudinally extending gap 320. In other embodiments (not shown), the cage body may include fewer or more than eight beam portions, and/or beam portions having a different or varying cross-section or shape. It can be seen that in this embodiment, four of the gaps 320 are formed through the middle of the four faces of cage body 308, and the other four gaps 320 are formed along the corner edges of cage body 308. Cage body 308 also includes eight circumferentially extending connector portions 322. The connector portions 322 interconnect the ends of the beam portions 318. Circular apertures 321 may be provided as shown between the ends of gaps 320 and the connector portions 322 to relieve stress concentrations at those locations as connector portions 322 flex. Four of the connector portions/flexures 322 are located at the proximal end 304 of cage body 308 (across the corner edges of cage body 308), and the other four connector portions/flexures 322 are located at the distal end 306 (across the distal end of the faces of cage body 308.) The connector portions 322 located at the proximal end 304 are staggered in relation to the connector portions 322 located at the distal end 306 such that each pair of adjacent beam portions 318 are connected at only one end by a connector portion 322. As with previously described embodiments, the beam portions 318 and connector portions 322 form a continuous serpentine or repeating S-shaped pattern. The beam portions 318 and or the connector portions 322 are configured to resiliently flex to allow the cage body 308 to increase in circumference when urged radially outward by plugs 310 and 312. When plugs 310 and 312 are not urging cage body 308 radially outward, the resiliency of beam portions 318 and or connector portions 322 allows cage body 308 to return to its original reduced circumference. It can be appreciated that as beam portions 318 and or connector portions 322 flex outwardly, gaps 320 become wider at their open ends opposite connector portions 322. The outwardly facing surfaces of beam portions 318 may each be provided with one or more points or spikes 323 as shown, to permit cage body 308 to grip the end plates of the vertebral bodies. In this exemplary embodiment, spiked or knurled surfaces are provided along the top and bottom of UEC 300 while the side surfaces are left smooth.

Figure 18:
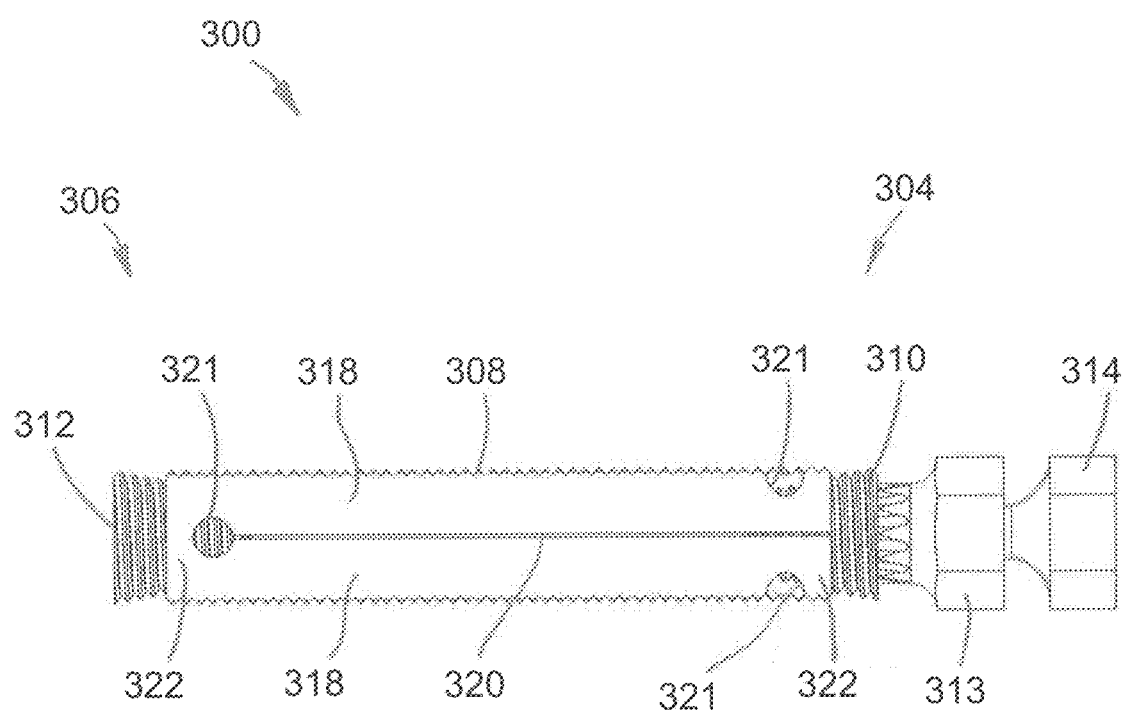
FIG. 18 is a side view showing the UEC of FIG. 16.
Figure 19A:
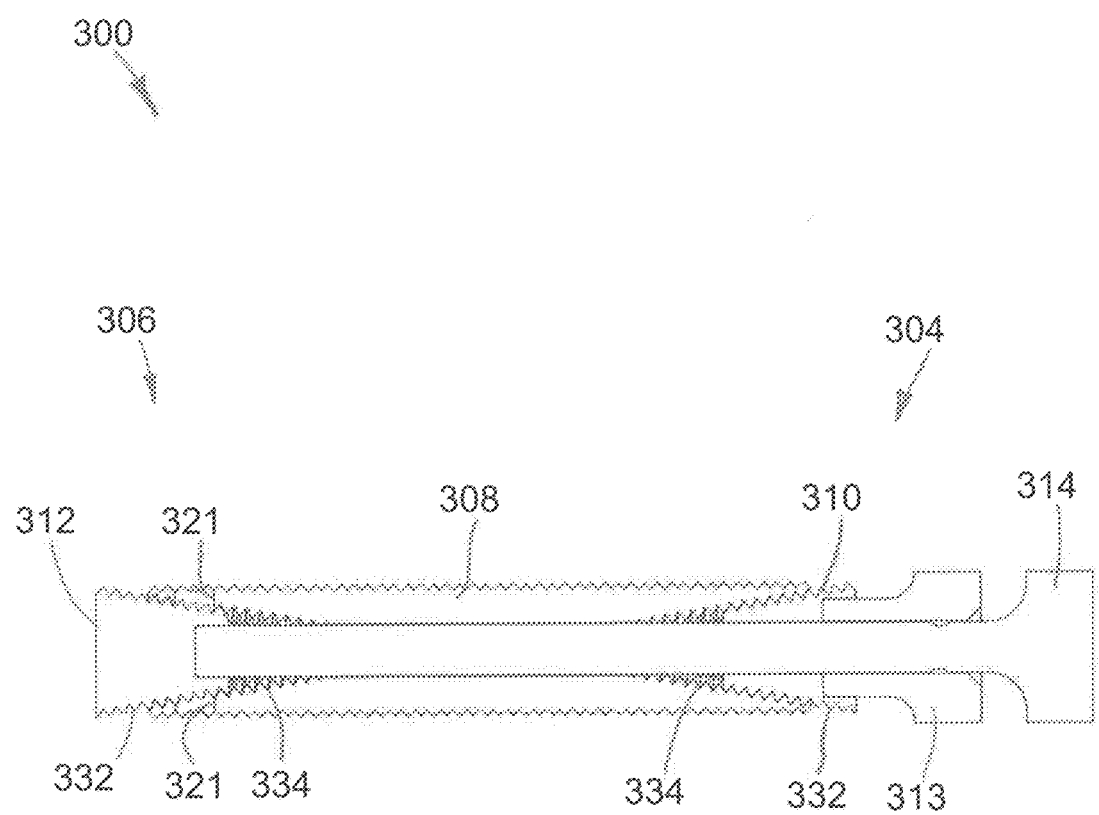
FIG. 19A is a side cross-sectional view showing the UEC of FIG. 16.
Figure 19B:
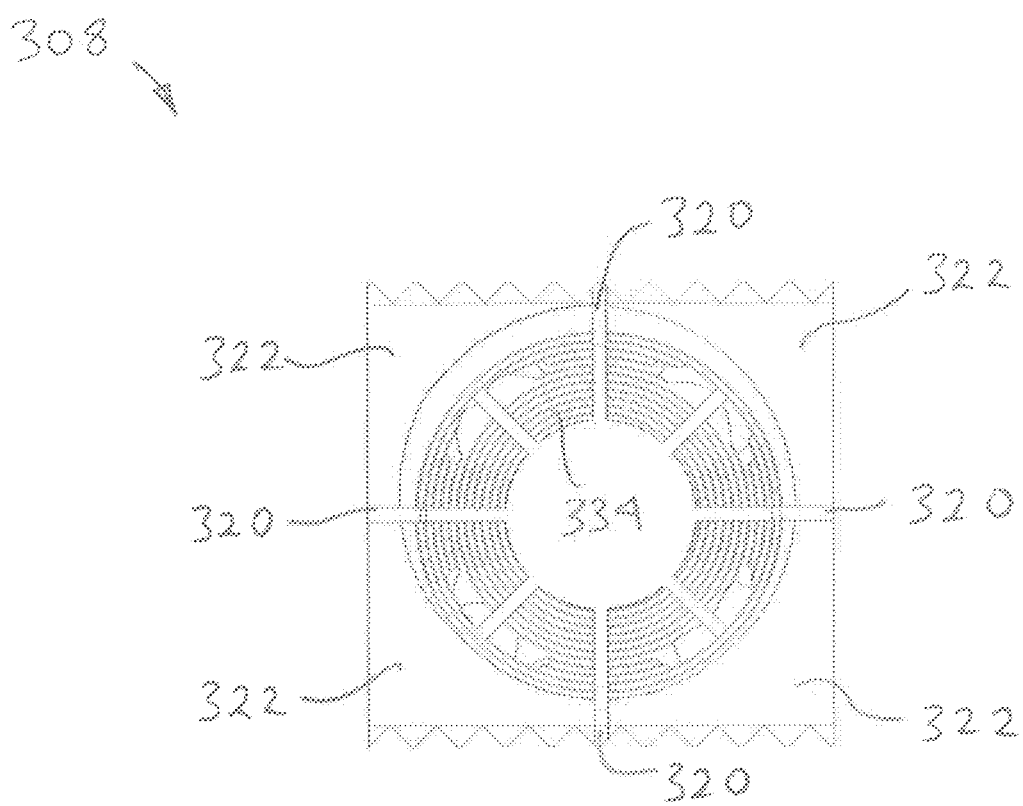
FIG. 19B is an end cross-sectional view showing the UEC of FIG. 16.

Referring to FIGS. 18 and 19, a side view and a side cross-sectional view, respectively, of UEC 300 are shown. In operation, the proximal end 304 of UEC 300 may be independently expanded by inserting proximal plug adjustment tool 313 into the mating recessed socket of proximal plug 310 (as shown in FIG. 19) and turning it clockwise. Turning proximal plug 310 clockwise causes the threaded ramped surfaces 332 of plug 310 to translate inwardly (to the left in FIGS. 18 and 19) along the threaded ramped surfaces 334 located along the inside of beam portions 318 and connector portions 322 to cause these elements to flex and expand radially outward as previously described. This process may be reversed by turning proximal plug 310 counterclockwise, thereby allowing the proximal end 304 of UEC 300 to return to its non-expanded state. Similarly, the distal end 306 of UEC 300 may be independently expanded by inserting a tool such as a five-lobed socket (not shown) through the central bore 325 in proximal plug 310 until it engages with the proximal end of actuator 314, which is attached to distal plug 312. Turning distal plug 312 counterclockwise (from the perspective of the proximal end) causes the threaded ramped surfaces 332 of plug 312 to translate inwardly (to the right in FIGS. 18 and 19) along the threaded ramped surfaces 334 located along the inside of beam portions 318 and connector portions 322 to cause these elements to flex and expand radially outward as previously described. This process may be reversed by turning distal plug 312 clockwise, thereby allowing the distal end 306 of UEC 300 to return to its non-expanded state.

Figure 20A:
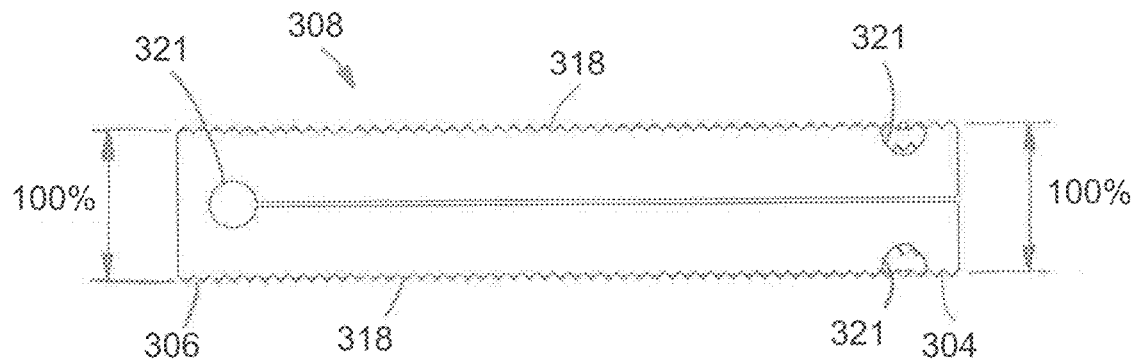
Figure 20B:
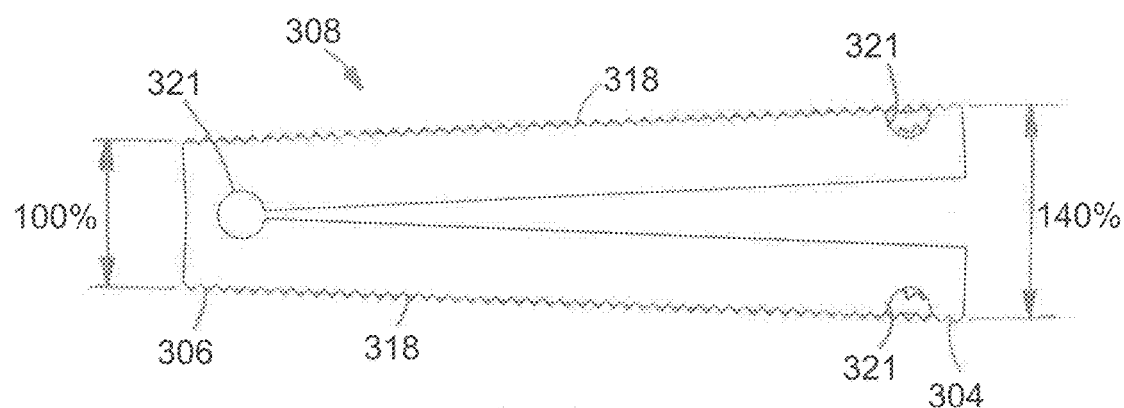
Figure 20C:
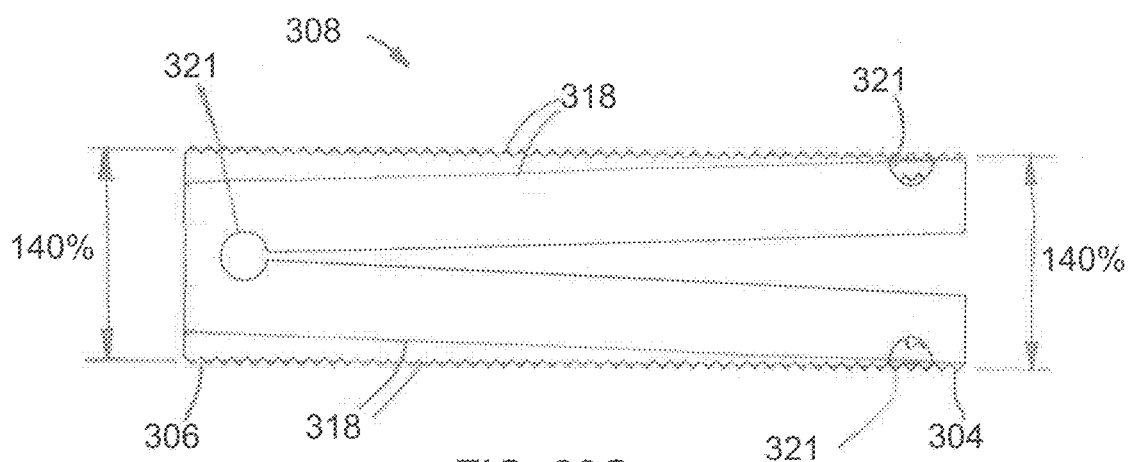

Referring to FIGS. 20A-20C, a series of sides views depicts the progression from a fully retracted and a fully expanded UEC 300. In FIG. 20A, cage body 308 is shown in a fully retracted position. In this figure, the height of each end of cage body 308 is labeled as 100% of retracted cage height. In FIG. 20B, the proximal end 304 of cage body 308 has been fully expanded while the distal end 306 remains fully retracted. In this exemplary embodiment, each end is capable of being expanded to a height (and therefore also a width) that is 140% of the fully retracted height, as shown. In FIG. 20C, the distal end 306 has also been expanded by 40%.

In some embodiments, UEC 300 has a cage length of 50 mm, an unexpanded cage height of 10 mm, and an expanded cage height of 14 mm. The overall length of UEC 300 with adjustment tools 313 and 314 in place and in the unexpanded state may be 75 mm. In other embodiments, the UEC may be configured to expand to about 11, 12, or 13 mm, or more than 14 mm. In still other embodiments, the UEC may be configured with dimensions larger or smaller than these to conform to a particular anatomy or procedure. In some embodiments, the UEC can form an included angle between its top and bottom surfaces of at least 20 degrees.

Figure 21:
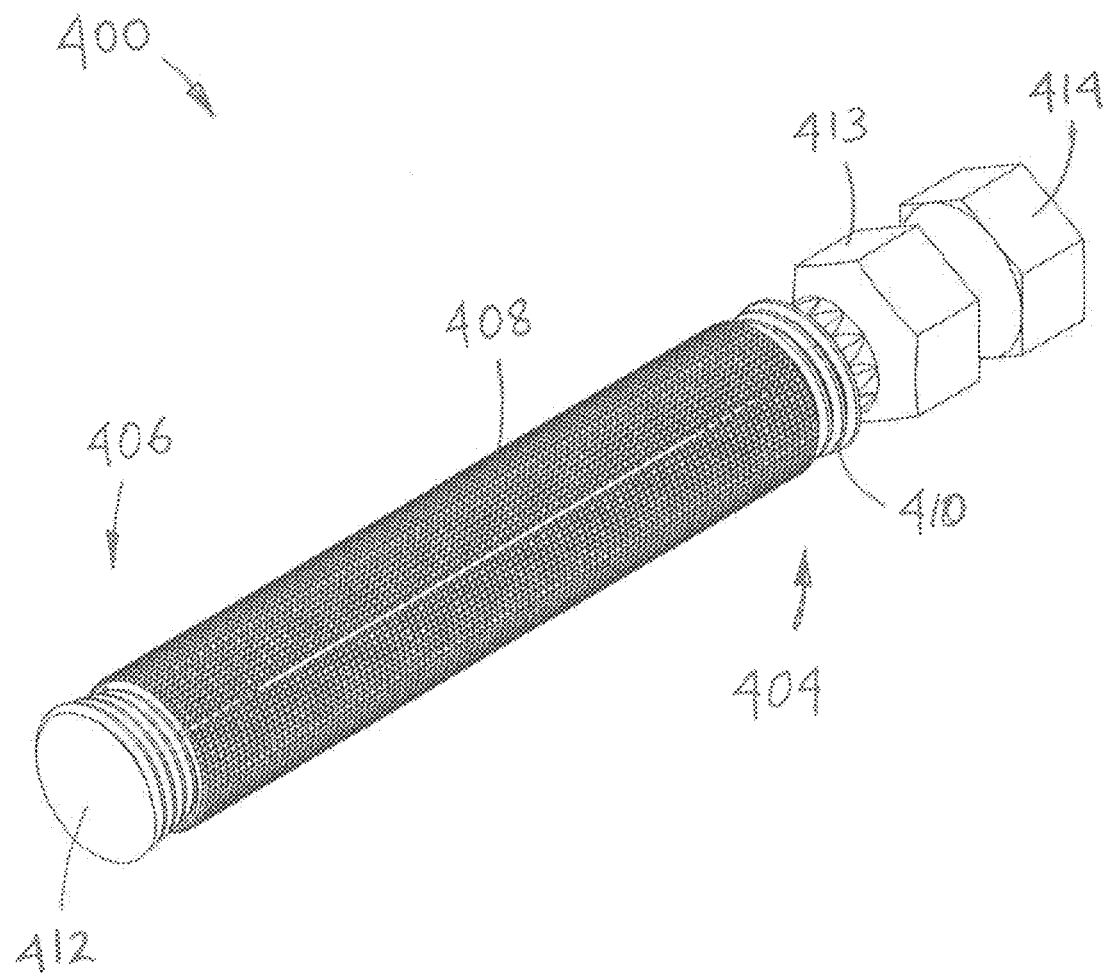
FIG. 21 is a perspective view of a fourth embodiment of a UEC in an unexpanded state according to aspects of the disclosure.
Figure 22:
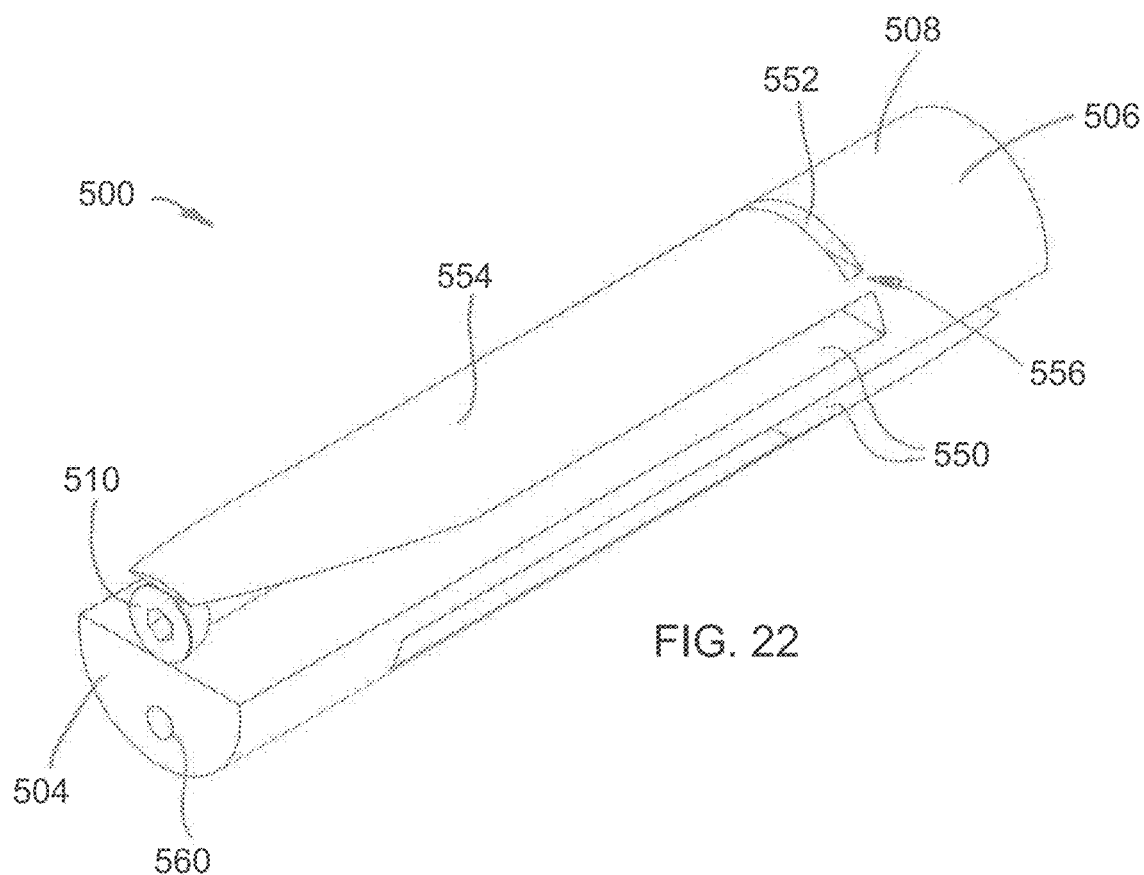
FIG. 22 is a perspective view of a fifth embodiment of a UEC in an unexpanded state according to aspects of the disclosure.

Referring to FIG. 21, a fourth embodiment of an exemplary UEC 400 according to aspects of the disclosure is shown. FIG. 21 is a perspective view which shows details of UEC 400. UEC 400 includes a proximal end 404, a distal end 406, cage body 408, proximal plug 410, distal plug 412, proximal plug adjusting tool 413, and distal plug adjusting tool 414. Other than cage body 408 having a circular cross-section rather than a square cross-section, UEC 400 is essentially identical in construction and operation to previously described UEC 300. In other embodiments (not shown), the UEC may have a cross-section transverse to the central longitudinal axis that is rectangular, trapezoidal, oval, elliptical or other shape.

Referring to FIGS. 22-25, a fifth embodiment of an exemplary UEC 500 according to aspects of the disclosure is shown. FIG. 16 is a perspective view which shows details of UEC 500. UEC 500 includes a proximal end 504 and a distal end 506, and shares many of the same features of previously described UECs 100-400, which are identified with similar reference numerals.

UEC 500 includes three components: a generally cylindrical, unitary cage body 508; a proximal actuator screw 510; and a distal actuator screw 512. The heads of actuator screws 510 and 512 may be referred to as plug members. Cage body 508 includes two longitudinal, off-center slots 550 which each extend about three-quarters of the length of cage body 508, and emanate from opposite ends and opposite sides of cage body 508. Cage body 508 is also provided with two transverse slots 552, each located adjacent to the closed end of one of the longitudinal slots 550. Each transverse slot 552 extends from the outer circumference of cage body 508 and approaches the base of a longitudinal slot 550. Each of the two pairings of a longitudinal slot 550 with a transverse slot 552 defines a cantilevered arm 554 that is connected with the remainder of the cage body 508 by a living hinge 556 near the closed ends of the two slots 550 and 552. Each living hinge 556 allows its associated arm 554 to flex outwardly against a vertebral body.

Figure 24:
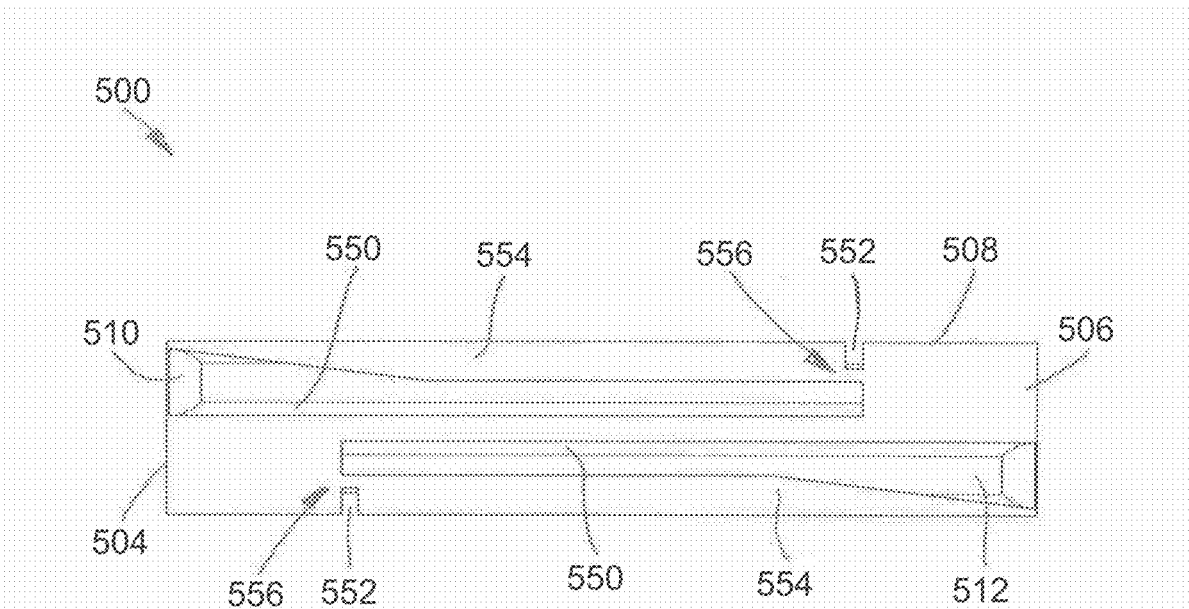
FIG. 24 is a side view showing the UEC of FIG. 22.
Figure 25:
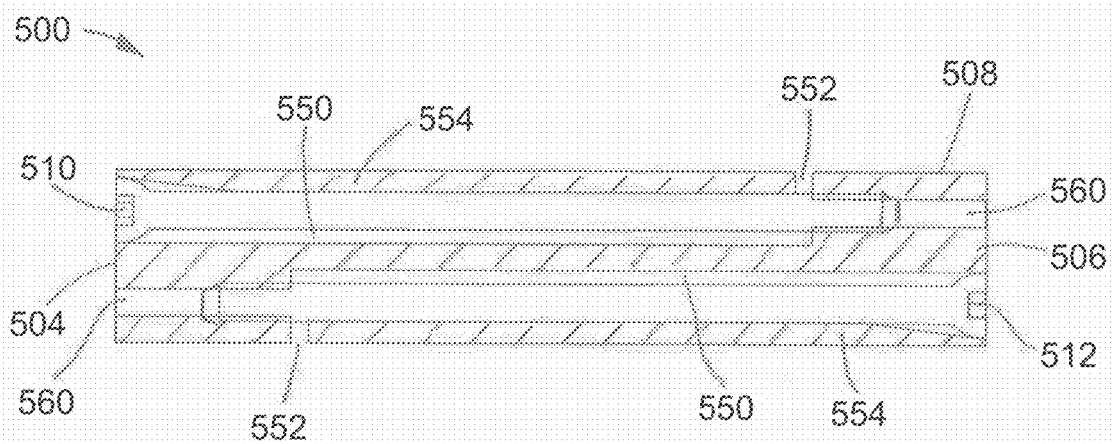
FIG. 25 is a side cross-sectional view showing the UEC of FIG. 22.

The open ends of longitudinal slots 550 are outwardly tapered to receive the enlarged, tapered heads of an actuator screw 510 or 512, as best seen in FIG. 24. The opposite ends of actuator screws 510 and 512 extend through longitudinal slots 550 and thread into the opposite ends of cage body 508. With this arrangement, each actuator screw 510 and 512 may be turned independently of the other, causing the screw to move axially relative to bone cage 508. This axial movement causes the head of the screw to urge the tapered tip of the associated arm 554 outward, or allowing it to flex back inward when the screw is turned in the opposite direction. If both actuator screws 510 and 512 are turned in the same direction the same amount, UEC 500 expands uniformly and increases the height between adjacent vertebral bodies. If one of the two actuator screws 510 or 512 is turned more than the other, the surgeon is able to change the angle between the vertebral bodies.

Figure 23:
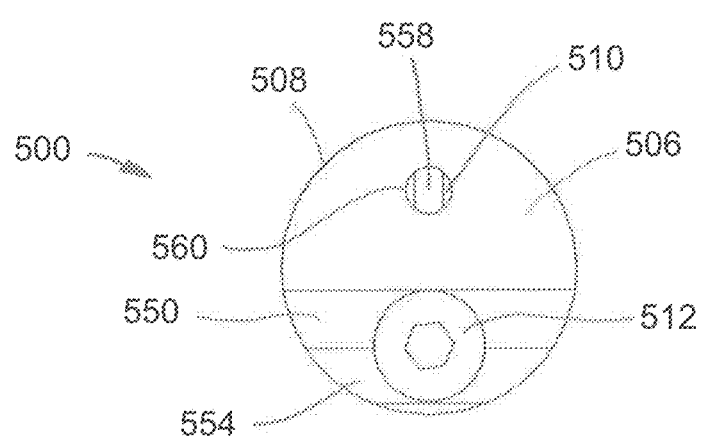
FIG. 23 is a distal end view showing the UEC of FIG. 22.

As best seen in FIG. 23, a slot 558 or other suitable feature may be provided in the end of each actuator screw 510 and 512 at the opposite end from the screw head. A hole 560 may also be provided through each end of cage body 508 to allow access to each of the two slots 558. This arrangement allows both of the actuator screws 510 and 512 to be turned from either end 504 and/or 506 of cage body 508.

Figure 26:
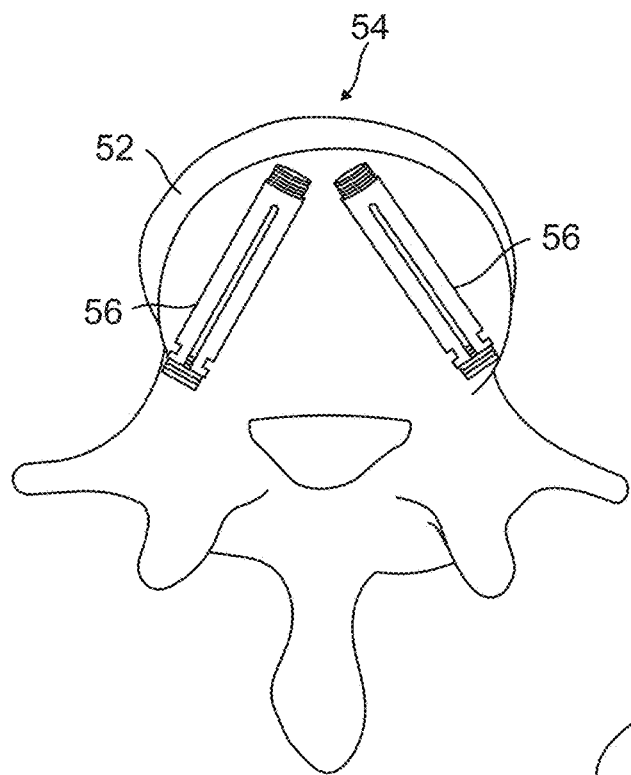
FIG. 26 is a cranial to caudal view showing the insertion sites of dual UECs on a vertebral body in one example implementation.
Figure 27:
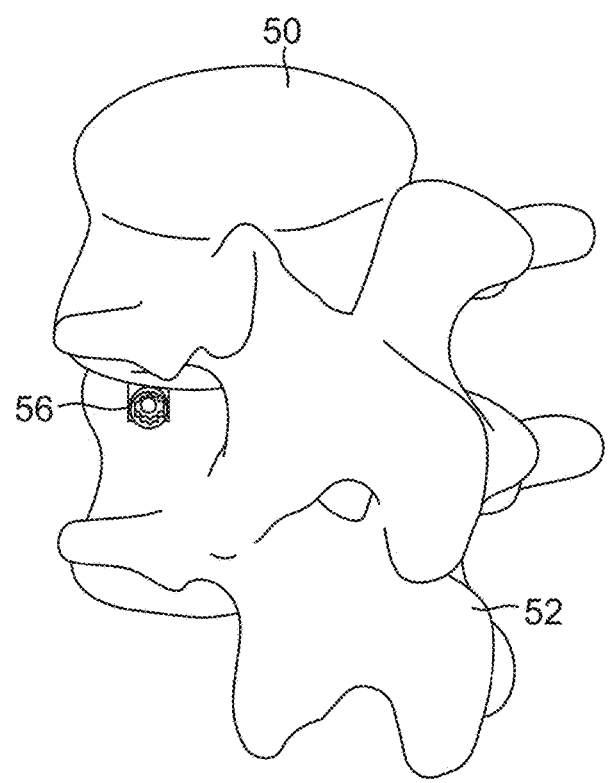
FIG. 27 is an oblique posterolateral view showing one of the insertion sites of the implementation of FIG. 26.
Figure 28:
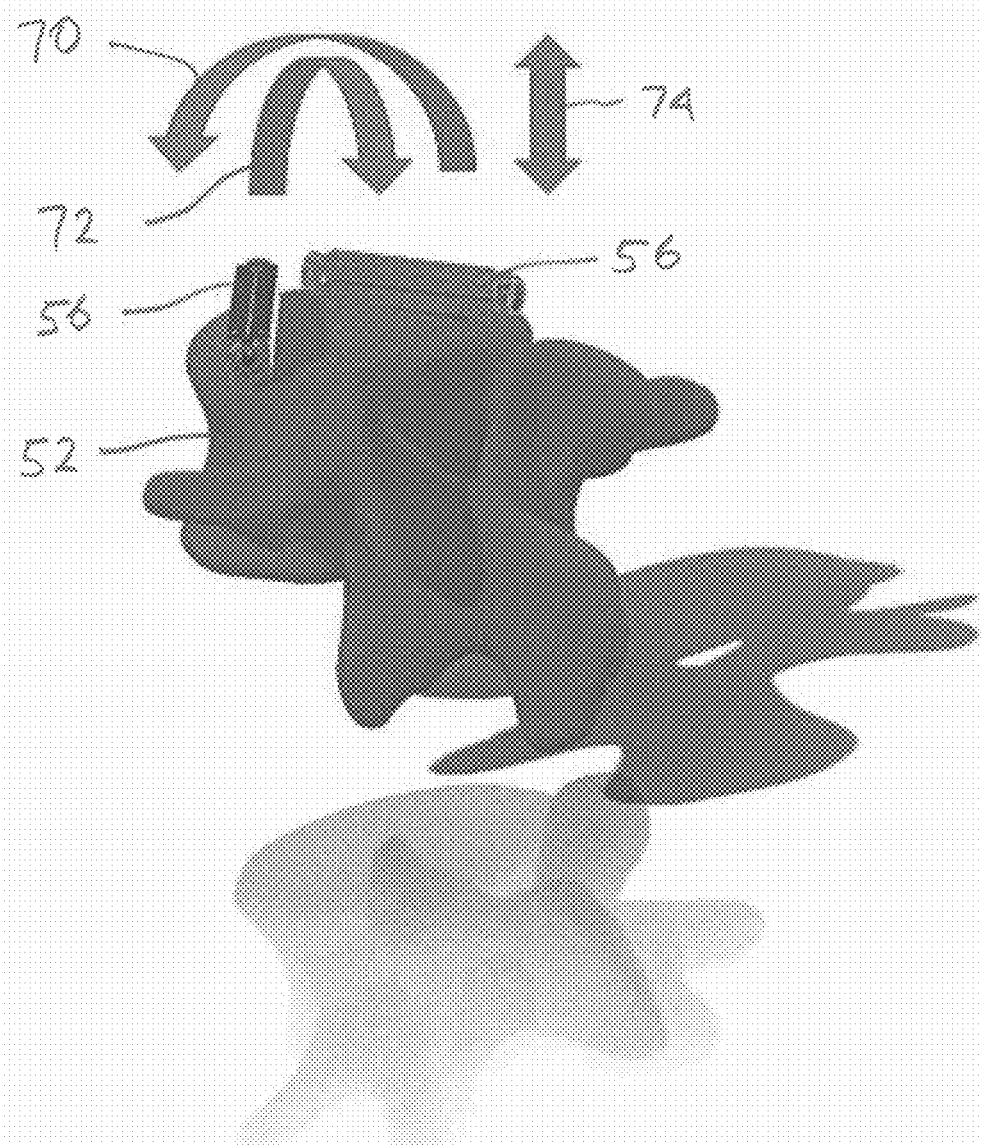
FIG. 28 is an oblique posterolateral view showing the axes of adjustment provided by the implementation of FIG. 26.

Referring to FIGS. 26-28, an example implementation utilizing two UECs 56 in tandem is shown. Each UEC 56 may be inserted as previously described in relation to FIGS. 1-3. In this implementation, UECs 56 are placed non-parallel to one another. As best seen in FIG. 28, this arrangement allows the surgeon to adjust the angle between the vertebrae about two different axes, and also translate the vertebrae with respect to one another about another axis.

Figure 29:
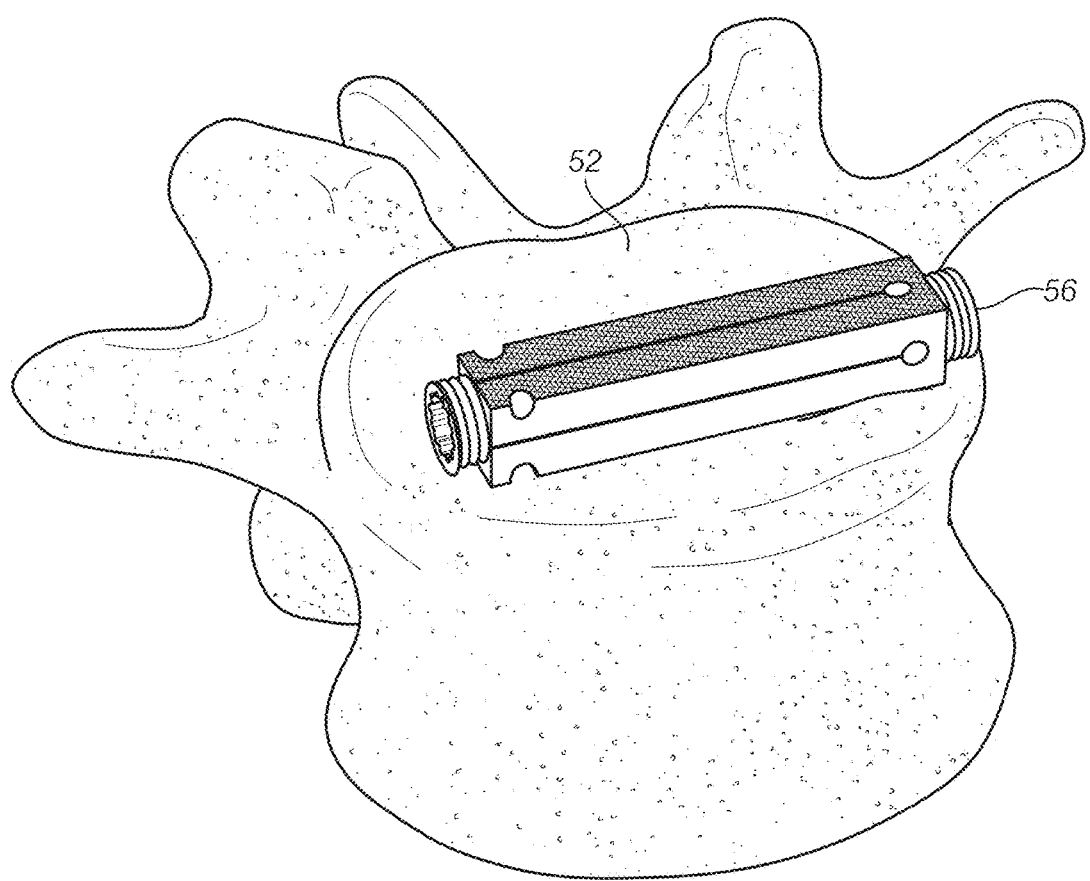
FIG. 29 is an oblique anterior view showing an anterior column implant.

FIG. 29 is an oblique anterior view showing placement of an anterior column implant 56 on a vertebral body 52. In this implementation, implant 56 is placed laterally across the vertebral body 52, forward of the lateral midline. After adjustment of implant 56, its plugs are flush with or recessed within the outer perimeter of the endplate of vertebral body 52 so as not to impinge upon adjacent tissue.

Referring to FIG. 30, a human spine 76 is shown that exhibits scoliosis. According to aspects of the disclosure, dual UECs may be placed at various levels of the spine to treat the condition. For example, a single UEC or pairs of UECs may be implanted at the levels depicted by reference numerals 78, 80, 82 and 84 shown in FIG. 30. By using the adjustments described above relative to FIG. 28, the curvature of the spine may be adjusted in three dimensions at these four levels to a correct alignment, as shown in FIG. 31.

Figure 32C:
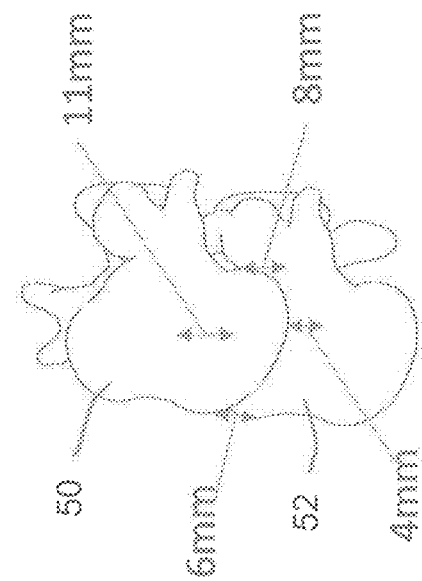
FIGS. 32A-32C are anterior, lateral and oblique views, respectively, showing adjacent vertebral bodies having misalignments/uneven spacing.
Figure 32A:
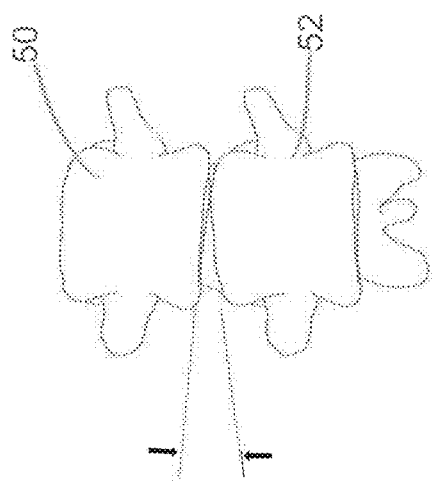
Figure 32B:
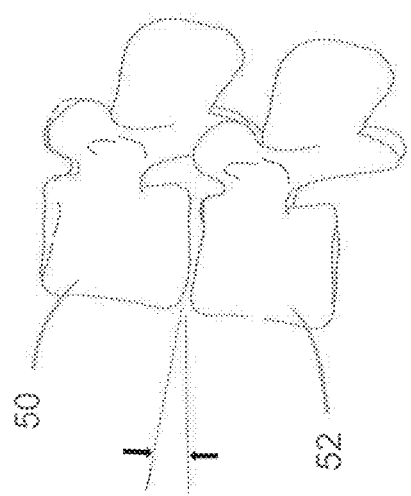

FIGS. 32A-32C are anterior, lateral and oblique views, respectively, showing adjacent vertebral bodies 50 and 52 having misalignments/uneven spacing.

Figure 33C:
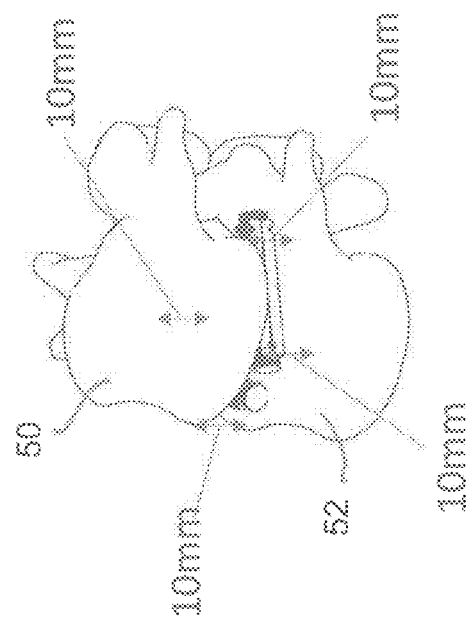
FIGS. 33A-33C are anterior, lateral and oblique views, respectively, showing the vertebral bodies of FIGS. 32A-32C with the misalignments/uneven spacing corrected according to aspects of the disclosure.
Figure 33A:
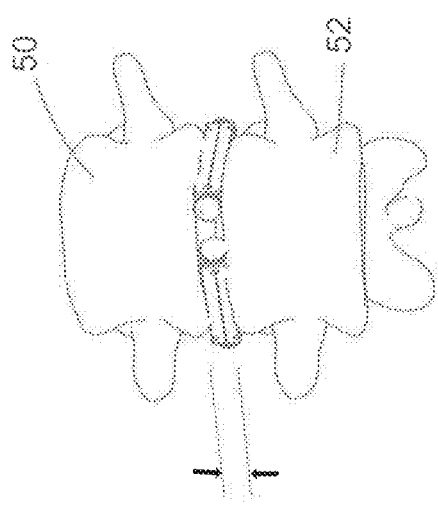
Figure 33B:
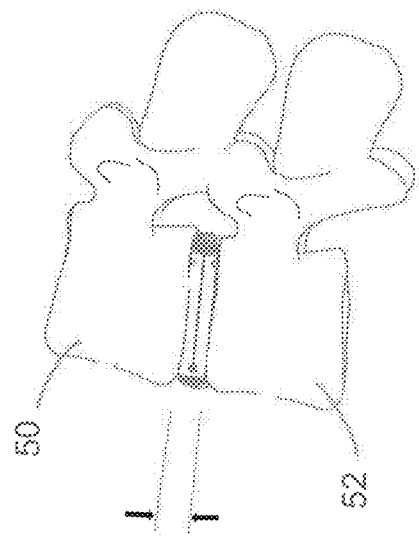

FIGS. 33A-33C are anterior, lateral and oblique views, respectively, showing the vertebral bodies 50 and 52 of FIGS. 32A-32C with the misalignments/uneven spacing corrected according to aspects of the disclosure.

The implants can be made of, for example, such materials as titanium, 64 titanium, or an alloy thereof, 316 or 321 stainless steel, biodegradeable and biologically active materials, e.g. stem cells, and polymers, such as semi-crystalline, high purity polymers comprised of repeating monomers of two ether groups and a ketone group, e.g. polyaryetheretherketone (PEEK)™, or Teflon™.

To prevent movement of proximal and distal plugs or actuators after implantation, in some implementations a biocompatible adhesive or thread locking compound may be applied to one or more of the moving parts. In some embodiments (not shown) a pin may be inserted radially or axially between the plug/actuator and the cage body to lock the parts in place post operatively. In some embodiments, a ratchet, spring loaded detent, or other locking mechanism may be provided for this purpose.

In general, as disclosed in the above embodiments, the cage body is cut with openings at every other end of each slot, like a sine wave, allowing expansion when the center of the cage becomes occupied with a cone or mandrill shaped unit. The cage body's series of alternating slots allows the expansion to take place while keeping the outside of the UEC one single piece. The slots plus the teeth on the surface allow for a solid grip on the bone surfaces and plenty of opportunities for good bone ingrowth. Also, by allowing the surgeon to make one end of the UEC thicker than the other, the effects of the cone (mandrill) introduction vary from uniform to selective conduit expansion. The UEC expansion mechanism is adaptable to both fixed fusion and mobile 'motion preservation' implants, with exteriors of the expanding implant per surgeon's choice (round, flat, custom, etc.) As such, in some implementations, relative motion may be preserved between the vertebral bodies adjacent the implanted UEC(s). In other implementations, it may be desirable to fuse the adjacent vertebral bodies around the implanted UEC(s).

To provide motion preservation between adjacent vertebrae, robust compressible materials may be used between the UEC and one or both of the vertebral endplates, and/or one or more components of the UEC may comprise such materials. These materials may replicate the load distributing and shock absorbing functions of the annulus and nucleus of a natural disk. For example, in some embodiments the UEC may be provided with tapered plugs made of a resilient polymer to allow the UEC to compress and expand to accommodate relative motion of the adjacent vertebrae. Examples of biocompatible materials suitable for some UEC embodiments include Bionate®, a thermoplastic polycarbonate-urethane (PCU) provided by DSM Biomedical in Exton, Pa., and ChronoFlex®, a PCU provided by AdvanSource Biomaterials in Wilmington, Mass.

The UEC provides advantages over currently existing technology that include correction of coronal plane deformity; introduction of interbody lordosis and early stabilization of the interbody space with rigidity that is greater than present spacer devices. This early stability may improve post-operative pain, preclude the need for posterior implants including pedicle screws, and improve the rate of successful arthrodesis. Importantly, the UEC provides improvement of space available for the neural elements while improving lordosis. Traditional implants are limited to spacer effects, as passive fillers of the intervertebral disc locations awaiting eventual fusion if and when bone graft in and around the implant fuses. By expanding and morphing into the calculated shape which physiologically corrects spine angulation, the UEC immediately fixes the spine in its proper, painless, functional position. As infused osteoinductive/osteoconductive bone graft materials heal, the patient becomes well and the implant becomes inert and quiescent, embedded in bone, and no longer needed.

In some embodiments, the external surface of the UEC may be 3D printed to not only fit into the intervertebral space per se, but to match the surface topography at each insertion location. In other words, a 3D printed endplate may be utilized, computer calculated to fit and expand the disc space of the individual patient, resulting in both best 'goodness of fit' for fusion, and improved axial skeletal alignment.

By creating to 'maps' that fit e.g. as a precisely congruent superior and inferior surface to fit into a particular patients disc space, and placing these UEC end plates on either side the novel UEC expansion mechanism, a patient's disc space AND overall spine alignment will be ideally treated toward best fusion (or motion preservation) and alignment.

"Method of Surgery" instructions may recommend the surgeon and/or robotic unit deploy expansion as programmed to insert the UEC into a particular disc level of pathology, to achieve best results. For example, preoperative patient scans/films can predict ideal UEC surgeon use, such as "turn Knob A a certain number of rotations clockwise," to maximize visible, palpable, and roentgenographic 'Goodness of Fit'. With this approach, post activation, the UEC implant fits the location, entering at the predetermined best angle (in 3 axes) using the proprietary Method of Surgery and UEC insertion tools provided.

In some embodiments, the UEC may be coated with hydroxyapatite. In some embodiments, toothed or 400 μm beaded surfaces may be utilized to promote bony ingrowth. Inflatable chambers may be provided within the endplate that can expand after being implanted. This approach addresses the 3-D congruence to proximate disc pathology. It can also allow for intervertebral arthrodesis or arthroplasty treatment and overall improved spinal alignment, integrating the internal proprietary expansion with the variable external endplate shapes and their contents. UEC inflatable endplates of polymer may be employed, such as tiny vacuoles, "bubblewrap", and multiple or singular bladder constructs. If a portion of the disk space were collapsed, that region could be aptly elevated or expanded by the UEC endplate variation in material and/or inflation. The inflatable chambers may contain compressible gas (such as air), granules as pharmacologics, and/or stem cells that are delivered via liquids. In cases where the UEC is compressible or force absorbing, the material and/or chamber could be used as a cushion or to 'selectively direct and protect chondrocytes' toward improvement of existing pathophysiology via best drug use or regeneration.

The 'preparation' of the UEC insertion site will vary per surgeon. In some implementations, an arthroscopic burr may be advisable for removing 0.5 mm of cortical bone along with all aberrant disc contents under digital arthroscopic camera control. In other implementations, the surgeon may just carefully curette the intervertebral space to 'clean it out' in preparation for the UEC implant insertion.

The UEC may be inserted directly into the insertion site, or may be inserted through proprietary or commercially available insertion tube. The insertion tube typically will have a blunt distal tip so that it can be inserted through an incision without causing tissue damage. The tube can be used with or without additional tissue retractors. The UEC may be preloaded into the insertion tube, or placed into the tube after the tube has been introduced into the insertion site. A pusher rod or other device may be utilized to deploy the UEC from the insertion tube into the insertion site. In some procedures, the placement of the UEC may be arthroscopically assisted.

Note that regardless of the endplate preparation, in the deformed, aging, pathologic spine there will be pathology to correct. According to various aspects of the present disclosure, the UECs provided herein may accomplish this in several ways as pertains to the external implant composition. For example, the UEC can expand as an externally threaded conduit, either uniformly end to end resulting in same diameters at each end post-operatively (such as 40% overall expansion), or precisely at either end, thus creating an overall conical albeit expanded UEC. Also, the UEC can be flat superiorly and inferiorly as shown in the above drawings, thus more likely matching the rather flat vertebral body end plates. However, according to further aspects of the present disclosure, special care should be taken to consider both the peripheral end plate boney rim as thicker more prominent cortical bone at the vertebral end plates with a sunken or concave thinner interior (thus subject to potential subsidence). The UEC MOS (Method of Surgery) contemplated herein considers the preoperative findings (e.g. MRI, 3D CT scan, X-rays) to integrate information on bone density, specific disc space and longitudinal spine anatomy, topography and alignment.

The various expanding cages disclosed herein and variations thereof are not limited to use in the spinal column but may be used between other bone segments throughout the human or animal body. For example, a UEC can be used during arthrodesis of a metatarsal joint. The UEC can aid in setting the orientation of the toe to a desired angle before fusion of the apposing bone segments occurs. Similarly, a UEC may be utilized in the knee, elbow or other body joints, or between two or more bone segments that have been fractured by trauma.

According to various aspects of the disclosure:
1) the UEC corrects spine surgical pathology both locally via horizontal (disc) and longitudinal vertical axial (scoliotic/kyphotic) spine deformity improvements.
2) the UEC is applicable cervical through lumbar for
    A) arthrodesis (fusion) or
    B) arthroplasty (motion preservation) or
    C) drug/cell therapy delivery
3) the UEC can expand uniformly throughout implant length, and/or expand only proximally (toward the surgical incision) or distally, thus enabling clinical adjustments favorable to spine diseased or injured patients for local and overall spondylopathies.
4) the UEC can be surgically inserted via outpatient MIS (Minimally Invasive—outpatient Surgery) as safe, efficacious implants "doing no harm" applying advantages from
    A) materials thicknesses for height differentials or
    B) expansion adjustments surgically controlled (before/during or after implantation) or via prefabricated portals or injections-programming implant 'mapped' corrections using
    C) polymers durometrically calculated with variable compressions, permanent or biodegradable activations at will.
    D) inflation of the implant as via UEC surface chambers or bladder(s).
    E) adding endplate biologics, foam, or other adaptables for best results.
    F) UEC expansion can adapt to expand variable external surface parameters including flat, round, or customized external maximally congruent surfaces to interface as with proximate endplates.

5) Delivery either via UEC materials per se (eluding substances-cells or pharmacologics) or through extrusion from a UEC container or delivery vesicle/depot/chamber/portal will enable not only immediate surgically correction but long term enhanced bone in growth and local/general therapeutic and/or regenerative clinical benefits.

While the disclosure has been described in connection with example embodiments, it is to be understood that the disclosure is not limited to the disclosed embodiments and alternatives as set forth above, but on the contrary is intended to cover various modifications and equivalent arrangements included within the claim scope.

The invention claimed is:

1. A method of 3D manufacturing an expandable implant comprising;
    preoperatively imaging at least one intervertebral disc space,
    manufacturing the implant, the implant comprising; a first endplate, a second endplate, an expandable proximal end, an expandable distal end, a first ramped surface and a second ramped surface, wherein expansion is capable of being independently effected relative to the first ramped surface, independently effected relative to the second ramped surface and independently effected relative to both the first ramped surface and the second ramped surface, and
    3D printing the first endplate, 3D printing the second endplate or 3D printing both the first endplate and second endplate.

2. The method of claim 1, wherein the implant is patient-specific.

3. The method of claim 1, wherein at least one endplate is 3D printed to fit a particular bone topography.

4. The method of claim 1, wherein the expansion relative to the first ramped surface is greater than the expansion relative to the second ramped surface.

5. The method of claim 1, wherein the expansion relative to the second ramped surface is greater than the expansion relative to the first ramped surface.

6. The method of claim 1, wherein the expansion relative to the first ramped surface is equal to the expansion relative to the second ramped surface.

7. The method of claim 1, wherein the implant comprises titanium.

8. The method of claim 1, wherein the implant is used in multiple horizontally affected intervertebral spaces.

9. The method of claim 1, wherein the implant is used in the treatment of lordosis, kyphosis and scoliosis.

10. The method of claim 1, wherein the preoperative imaging comprises MRIs, 3D CT scans, or X-rays.

11. The method of claim 1, wherein the expandable implant further comprises a first actuator and a second actuator wherein when one of the first actuator or the second actuator is rotated in a first direction and causes an expansion of the distal end of the cage body and when rotated in a second direction causes a contraction of the distal end of the cage body.

12. The method of claim 1, wherein the expandable proximal end is independently expandable from the expandable distal end.

13. The method of claim 1, further providing instructions for expanding solely the proximal end, instructions for expanding solely the distal end and instructions for cooperatively expanding both the proximal end and distal end.

14. A method of 3D manufacturing an expandable implant comprising;
    pre-operatively imaging at least one intervertebral disc space,
    3D printing an expandable implant wherein the outer surface is 3D printed for fitting into the at least one intervertebral disc space, and
    providing instructions comprising; a method of implanting an expandable implant, turning a first actuator to adjust the expansion or contraction of a proximal end of the expandable implant, turning a second actuator to adjust the expansion or contraction of a distal end of the expandable implant, and turning both the first actuator and the second actuator to adjust the cooperating expansion or contraction of both the proximal end and distal end of the expandable implant.

15. The method of claim 14, wherein expansion or contraction of the proximal end is independent from the expansion or contraction of a distal end.

16. The method of claim 14, wherein the height and/or angle of the implant may be adjusted.

17. The method of claim 14, wherein the turning of the first actuator independently effects expansion or contraction of the proximal end relative to a ramped surface.

* * * * *